US008614262B2

(12) United States Patent
Bublewitz et al.

(10) Patent No.: US 8,614,262 B2
(45) Date of Patent: *Dec. 24, 2013

(54) CURABLE COMPOSITIONS, CURED PRODUCTS PRODUCED THEREFROM AND USE THEREOF

(75) Inventors: Alexander Bublewitz, Herborn (DE); Jens-Peter Reber, Meinerzhagen (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 214 days.

This patent is subject to a terminal disclaimer.

(21) Appl. No.: 12/776,054

(22) Filed: May 7, 2010

(65) Prior Publication Data

US 2011/0118378 A1 May 19, 2011

(30) Foreign Application Priority Data

May 9, 2009 (DE) .......................... 10 2009 021 553

(51) Int. Cl.
*A61K 6/10* (2006.01)
(52) U.S. Cl.
USPC ................................ 523/109; 264/16; 106/35
(58) Field of Classification Search
USPC ................................ 523/109; 264/16; 106/35
See application file for complete search history.

(56) References Cited

U.S. PATENT DOCUMENTS

| | | | |
|---|---|---|---|
| 2,915,544 A * | 12/1959 | Holbrook et al. ............. | 556/459 |
| 4,353,242 A | 10/1982 | Harris et al. | |
| 4,657,959 A * | 4/1987 | Bryan et al. .................. | 524/266 |
| 4,965,295 A | 10/1990 | Schwabe et al. | |
| 5,064,891 A | 11/1991 | Fujiki et al. | |
| 5,249,862 A | 10/1993 | Herold et al. | |
| 5,286,105 A | 2/1994 | Herold et al. | |
| 5,367,001 A | 11/1994 | Itoh et al. | |
| 5,419,460 A | 5/1995 | Herold et al. | |
| 5,569,691 A | 10/1996 | Guggenberger et al. | |
| 5,596,025 A * | 1/1997 | Oxman et al. ................. | 523/109 |
| 5,597,882 A | 1/1997 | Schiller et al. | |
| 5,750,589 A | 5/1998 | Zech et al. | |
| 5,907,002 A | 5/1999 | Kamohara et al. | |
| 6,129,244 A | 10/2000 | Horth | |
| 6,168,052 B1 | 1/2001 | Keller | |
| 6,291,546 B1 | 9/2001 | Kamohara et al. | |
| 6,455,029 B1 | 9/2002 | Angeletakis et al. | |
| 6,649,146 B2 | 11/2003 | Angeletakis et al. | |
| 6,677,393 B1 | 1/2004 | Zech et al. | |
| 6,861,457 B2 | 3/2005 | Kamohara | |
| 6,884,828 B2 | 4/2005 | Schaub et al. | |
| 7,230,140 B2 | 6/2007 | Shirakawa et al. | |
| 2001/0039323 A1 | 11/2001 | Achenbach et al. | |
| 2008/0319100 A1 * | 12/2008 | Bublewitz et al. ........... | 523/109 |

FOREIGN PATENT DOCUMENTS

| | | |
|---|---|---|
| DE | 3410646 A1 | 3/1984 |
| DE | 3410646 A1 | 10/1985 |
| DE | 4010281 A1 | 4/1990 |
| DE | 4010281 A1 | 10/1990 |
| DE | 4306997 A1 | 3/1993 |
| DE | 4137698 A1 | 5/1993 |
| DE | 4306997 A1 | 9/1994 |
| DE | 19922929 A1 | 5/1999 |
| DE | 19922929 A1 | 11/1999 |
| DE | 69917384 T2 | 1/2000 |
| DE | 10017154 A1 | 4/2000 |
| DE | 10017154 A1 | 11/2001 |
| DE | 102006001126 * | 7/2007 |
| DE | 102006001126 A1 | 7/2007 |
| EP | 0170219 A2 | 2/1986 |
| EP | 0231420 A1 | 8/1987 |
| EP | 0492412 A1 | 7/1992 |
| EP | 0492413 A1 | 7/1992 |
| EP | 0541972 A1 | 5/1993 |
| EP | 0613926 A2 | 3/1994 |
| EP | 0729341 A1 | 9/1995 |
| EP | 0723807 A2 | 7/1996 |
| EP | 0729341 A1 | 9/1996 |
| EP | 0847745 A2 | 6/1998 |
| EP | 0885392 A2 | 6/1998 |
| EP | 0885932 A2 | 12/1998 |
| EP | 0956908 A1 | 11/1999 |
| EP | 0244478 B1 | 4/2000 |
| EP | 0864643 B1 | 7/2001 |

(Continued)

OTHER PUBLICATIONS

Rupp, et al., Deutsch Zahnarztliche Zeitschrift, "Quantifizierung der Benetzungs-eigenschaften von hydrophilierten A—Silikonen und Polyethern wahrend der applikationsphase", 60 (2005) 10, pp. 587-592.

(Continued)

*Primary Examiner* — James J Seidleck
*Assistant Examiner* — Peter A Salamon
(74) *Attorney, Agent, or Firm* — McDonnell Boehnen Hulbert & Berghoff LLP

(57) ABSTRACT

A composition containing curable polymers is disclosed selected from the group of organopolysiloxanes that crosslink by means of an addition reaction, organopolysiloxanes that crosslink by means of a condensation reaction, polyethers that contain alkoxysilyl groups and crosslink by means of a condensation reaction, polyethers that contain aziridino groups and crosslink by means of an addition reaction, polyethers that contain alkenyl groups and crosslink by means of an addition reaction, polyethers that contain ester groups of an ethylenically unsaturated carboxylic acid and crosslink by means of a radical polymerization reaction, or polyethers, silicones or rubbers that crosslink by means of a ring-opening metathesis reaction and also contain at least one nonionic and/or ionic fluorosurfactant.

30 Claims, No Drawings

(56) References Cited

FOREIGN PATENT DOCUMENTS

| | | |
|---|---|---|
| EP | 1165016 A1 | 1/2002 |
| EP | 1226808 A2 | 7/2002 |
| EP | 1290998 A1 | 3/2003 |
| EP | 1317917 A1 | 6/2003 |
| EP | 0974626 B1 | 5/2004 |
| WO | 9844860 A1 | 10/1998 |
| WO | 00/48553 A1 | 8/2000 |
| WO | 0232338 A2 | 4/2002 |
| WO | 2004/058196 A1 | 7/2004 |
| WO | 2005000147 A1 | 1/2005 |
| WO | 2005/016289 A1 | 2/2005 |
| WO | 2007/080071 A2 | 7/2007 |

OTHER PUBLICATIONS

Ullmann Encyclopadie der Technischen Chemie, Band 21, Seite 523.

* cited by examiner

CURABLE COMPOSITIONS, CURED PRODUCTS PRODUCED THEREFROM AND USE THEREOF

Novel curable compositions are described, being suitable in particular for use as dental impression compounds and being characterized by very good wetting behavior and by very good biodegradability.

Dental impression compounds are known per se and have already been in use for a long time. These compounds must have a variety of properties, such as rapid setting behavior, excellent precision of detail and at the same time good shelf-life of the precursors. Two-component mixtures, which are blended together immediately before use and then must be processed rapidly, are generally used. To achieve the best possible precision of detail, it is important for the smallest possible amount of fluid such as saliva or blood to be between the tooth and/or gingiva on the one hand and the impression being formed on the other hand, and absorption of this fluid into the impression being formed must be minimal.

Dental impression compounds usually contain hydrophobic materials, such as polyorganosiloxane. There have already been proposals for using surfactants in dental impression compounds to minimize the layer of liquid between the impression and the tooth or gingiva. These cause the film of water to be distributed and therefore make it difficult for a film of liquid to develop.

U.S. Pat. No. 4,657,959 describes a curable silicone composition, which can be used as a dental impression material and contains a curable silicone prepolymer and a surfactant. The surfactant to be used is preferably an ethoxylated nonionic surface-active agent containing one or more siloxane groups or perfluoroalkyl groups. The surfactant is used in an amount such that, 3 minutes after applying a droplet of water to the cured composition, the composition especially preferably has a contact angle of <10°. However, these contact angle properties on impression materials that are already cured after 3 minutes do not meet the demands of actual practice. In addition, amphoteric or ionic fluorosurfactants are mentioned in the examples in this U.S. Pat. No. 4,657,959, and in the case of the nonionic fluorosurfactants, the perfluoroalkyl groups are linked to the polyether groups by an $SO_2NR$ group. These $SO_2NR$ groups are unsuitable for use in a platinum-catalyzed silicone that crosslinks by means of an addition reaction because they develop a lot of metal chelate complexes on the platinum catalyst and thereby inhibit the latter. Furthermore, U.S. Pat. No. 4,657,959 does not disclose either the addition of an unreactive polyether polymer or of a reactively polymerizable polyether polymer, e.g., having vinyl, allyl or SiH groups.

EP-A-1 290 998 describes a silicone impression compound that crosslinks by means of an addition reaction and contains at least 2 aliphatically saturated hydrocarbon groups, a polyether having at least one alkyl group, an organohydrogen siloxane, a soluble platinum catalyst, an inorganic filler and a nonionic surfactant and/or a polyether-modified silicone oil.

EP-A-0 847 745 describes dental silicone impression materials, which, in addition to containing silicone polymers having SiH groups and silicone polymers having Si-alkylene groups, catalysts and inorganic fillers, also contain a polysiloxane-polyester polymer having at least one (poly)alkylene oxide substituent based on dimethicone and having one fluorinated alkyl substituent. According to this disclosure, a contact angle of less than 73° is determined by the Wilhelmi method on a cured solid sample body. The fluorinated polysiloxane polyester used here is a high-molecular polymer having fluorinated hydrocarbons on each chain terminus. The contact angles tend to be small. The fluorinated polysiloxane polyester is not a traditional low-molecular surfactant with a hydrophilic head and a hydrophilic tail because of the polymer structure, the high-molecular weight of the polymers and the fluorocarbon groups on both chain termini.

WO-A-2004/058196 describes dental impression material comprising a polyvinylsiloxane and a surfactant, where the surfactant imparts a wettability to the composition such that 15 minutes after curing, the material has a surface contact angle of less than approximately 10° with water about 15 seconds later. In particular these contact angles are achieved by using the PEG-8 methicone surfactant.

EP-A-1 165 016 describes an impression material that crosslinks by means of an addition reaction based on silicone with a (poly)alkylene oxide and/or derivatives thereof with a molecular weight >3000 g/mol with a concentration between 0.001 and 1.0 wt %. The polyether used should improve the stability of the impression material. At the same time, the contact angles were found to be >80°. This document shows that when only polyether is added, the good contact angle achieved is not good, and therefore good hydrophilic properties are not achieved.

EP-A-0 729 341 discloses the use of polyether carbosilanes for hydrophilization of dental impression compounds. The contact angle/surface angle measurement is performed 30 minutes after curing the impression material and the contact angles are at least 42°.

EP-A-0 613 926 describes polyether impression materials containing at least one hydrophilic agent from the group consisting of hydrophilic silicone oils, fluorinated hydrocarbons, block copolymers of ethylene oxide/propylene oxide, fatty alcohol derivatives, alkylphenol derivatives, fatty amines, amine oxides, fatty acid glycol and glycerol derivatives, fatty acids and fatty acid monoesters. The contact angle measurement is performed 30 minutes after curing of the impression material and the contact angles are between 18° and 65°.

WO-A-00/48553 describes an impression material composition that crosslinks by means of an addition reaction and contains a polymerizable silicone polyether with comb-like polyether groups. Combinations of this polymerized silicone polyether with nonylphenyl ethoxylate surfactants were described in the examples.

EP-A-0 231 420 discloses a silicone impression material that crosslinks by means of an addition reaction and contains a silicone polyether.

DE-A-40 10 281 discloses polyether impression compositions which crosslink by means of an addition reaction and in which the polyether has terminal vinyl dimethylsiloxy groups or allyl groups. The unsaturated groups bound to the polyether by an SiOC bond are susceptible to hydrolysis and are not stable in storage. Otherwise, the polyethers are linked to vinyl dimethylsiloxane groups by Pt-catalyzed hydrosilylation. The highly active catalyst cannot be separated by conventional purification methods. Even purification of the polymer by high vacuum distillation is impossible because of the high molecular weights of the polymer and the Pt catalyst. The polyether polymers contaminated with residual platinum and synthesized in this way are not stable in storage and therefore are not suitable for a dental impression compound composition. For this reason, there has not been any commercialization of these products to this day.

U.S. Pat. No. 5,064,891 describes a silicone composition, which contains a silicone surfactant and crosslinks by means of an addition reaction. The contact angle measurements were performed on cured sample bodies 3 minutes after applying the water droplets. The contact angles described are between 60° and 65°.

EP-A-0 885 932 describes organopolysiloxane compositions which crosslink by an addition reaction and contain a hydrophilic unsaturated polysiloxane-polyether copolymer having 2 to 5 silicon atoms and at least one aliphatic unsaturated functionality and at least one polyether functionality.

U.S. Pat. No. 5,907,002 describes a silicone impression material which crosslinks by means of an addition reaction and is formulated as a combination of a nonionic surfactant with a methyl phenyl polysiloxane. The nonionic surfactant may have a lipophilic group in addition to the hydrophilic group, and the lipophilic group may be an alkyl group or a fluorocarbon group. The use of mixtures of silicone surfactant with a fluorosurfactant is not disclosed. The contact angles achieved are between 28° and 60°.

Combinations of fluorosurfactants and silicone surfactants are known from DE 699 17 384 T2 (corresponding to EP-B-0 974 626). This document describes aqueous pigmented ink jet printer inks containing such surfactant mixtures.

Finally, DE-A-199 22 929 describes curable dental impression materials containing surfactants or combinations of surfactants. These impression materials are intended for making molds of the oral mucosa and they flow at a very low pressure but they do not flow when no pressure is applied. The impression material should cause very little irritation of the oral mucosa. The use of mixtures of silicone surfactants and fluorosurfactants is not disclosed.

U.S. Pat. No. 6,861,457 describes hydrophilic dental impression materials based on polysiloxanes, which crosslink by means of an addition reaction and which contain, in addition to a polyether with unsaturated groups, a nonionic surfactant or a polyether-modified silicone oil. This document does not describe combinations of fluorosurfactants with silicone surfactants.

DE-A-43 06 997 discloses hydrophilized polyethers which may contain a wide variety of surfactants. In addition to other surfactants, hydrophilic silicone oils or fluorinated hydrocarbon compounds are disclosed as possible substance classes. Curable compositions containing aziridino group-capped polyethers and a nonionic fluorosurfactant (Fluorad FC430) are described in the examples. According to the 3M Material Safety Data Sheet, edition 30, August 2002, this compound contains perfluoroctylsulfonate groups. DE-A-43 06 997 does not disclose any curable compositions containing mixtures of silicone surfactants and fluorosurfactants with (poly)alkylene oxide groups, carbohydrate groups or aliphatic polyhydroxy groups.

EP-B-0 244 478 describes the use of hydrophilic silicones as dental impression materials. This document discloses, among other things, the use of wetting agents of ethoxylated nonionic surfactant substances with solubilizing siloxane or perfluoroalkyl groups. This document does not describe any curable compositions containing mixtures of silicone surfactants and fluorosurfactants with (poly)alkylene oxide groups, carbohydrate groups or aliphatic polyhydroxy groups.

WO-A-2005/016289 describes dental impression compounds based on polyorganosiloxanes, which are characterized by the presence of a wetting agent that improves the wettability of the compound by water, so that after 3 minutes a contact angle of less than 50° is established. For example, ethoxylated nonylphenols or PEG-8 methicone are proposed as wetting agents.

In the patent documents cited, the contact angle measurements are not based on practical requirements, i.e., the contact angles are measured on cured sample bodies. However, according to practical requirement, first of all the contact angle properties of the cured impression material are not relevant, but on the contrary, the contact angle properties of the uncured plastic state are critical, and furthermore, the contact angle properties are not only relevant after a period of 3 minutes, but rather immediately in taking the impression, i.e., between >0 seconds and <10 seconds after the initial contact between the plastic impression material and the dental substance and/or the oral mucosa. This is explained by the fact that the impression material must cause wetting of the moist saliva-wetted dental substance and oral mucosa initially, i.e., between >0 seconds and <10 seconds, and must immediately flow onto it in taking the dental impression during the processing time, i.e., in the uncured state. Anything which occurs thereafter in time in terms of contact angle properties is no longer relevant for a dental impression that is to be faithful to details.

In the phase after mixing the two components, the so-called processing time, which is important for the flow of the impression material onto the moist tooth under practical conditions, when the impression material is still plastically deformable and comes in contact with moist teeth, saliva and blood, the materials disclosed in the prior art documents described above do not have a good contact angle of ≤10°. No spreading of a droplet of water on the surface of the material is observed. The contact angles described in these documents are relevant only in casting the cured impression outside of the mouth with liquid plaster slurry to prepare the model, but are not relevant in the critical taking of an impression in the mouth. Furthermore, none of these documents describe the use of a synergistic surfactant mixture or a combination of this mixture with a polyether.

A very up-to-date and scientific investigation by Rupp et al. in *Deutsche Zah-närztliche Zeitschrift* [German Dental Journal], 60 (2005) 10, pages 587-592 describes the requirements of a dental impression material with regard to wetting behavior. This involved conducting investigations of the initial hydrophilicity and equilibrium hydrophilicity. A practical requirement resulting from these investigations is that the impression material should have a low initial hydrophilicity at all times during the plastic phase of the processing time and additionally should have an equally low equilibrium hydrophilicity at all times.

Under practical conditions, the application and flow of the impression material in a patient's mouth will take place at different points in time, depending on the impression technique and the number of teeth of which impressions are to be taken. For example, a relatively short time, e.g., 40 seconds, is required for application and flow in the case of a single crown impression, whereas the application and flow are completed only after 2 minutes in the case of more extensive inlets with 4 or 5 teeth of which impressions are to be made.

According to the investigation by Rupp et al., the impression materials used today, especially the silicone impression materials, have a marked drift in the hydrophobic direction with an increase in processing time, which runs against the aforementioned practical requirements and practical demands of the impression material.

In addition, the initial hydrophilic contact angles measured there also need improvement in the case of both polyether and silicone impression materials.

Dental impression compounds having significantly improved wetting behavior are known from WO 2007/080071 A2. This document discloses various crosslinkable systems containing a synergistic combination of selected silicone surfactants and selected fluorosurfactants.

Based on this prior art, the object of the present invention was to provide a curable composition, which is suitable preferably as a dental impression compound that yields a low initial contact angle and a constant and low equilibrium contact angle (hydrophilic) at all times during the processing time (both at the beginning and at the end), so that under practical conditions, extremely good flow onto the moist tooth and/or gum tissue is achieved, which in turn leads to the development of an impression that is extremely faithful in the details and on the other hand is highly biodegradable.

It has surprisingly been found that this object is achieved by the use of selected fluorosurfactants in combination with a nonionic surfactant having silicon-containing groups in selected crosslinkable systems.

The present invention relates to a composition containing curable polymers selected from the group of organopolysiloxanes that crosslink by means of an addition reaction, organopolysiloxanes that crosslink by means of a condensation reaction, polyethers that contain alkoxysilyl groups and crosslink by means of a condensation reaction, polyethers that contain aziridino groups and crosslink by means of an addition reaction, polyethers that contain alkenyl groups and crosslink by means of an addition reaction, polyethers that contain ester groups of an ethylenically unsaturated carboxylic acid and crosslink by means of a radical polymerization reaction or polyethers, silicones or rubbers that crosslink by means of a ring-opening metathesis reaction; also containing at least one nonionic and/or ionic fluorosurfactant, selected from the group of a) fluorosurfactants, which have at least one partially fluorinated or perfluorinated alkylene oxide or (poly)alkylene oxide unit,
b) fluorosurfactants, which have, in addition to an ionic group, a partially fluorinated or perfluorinated alkyl group with fewer than 5 carbon atoms,
c) fluorosurfactants, which have, in addition to an ionic group, a partially fluorinated or perfluorinated alkoxyalkylene group with fewer than 5 carbon atoms,
d) fluorosurfactants, which have, in addition to an ionic group, a partially fluorinated alkyl group with at least 5 carbon atoms, wherein only ω-mono-, di- or trifluoromethyl groups or ω-mono-, di-, tri-, tetra- or penta-fluoroethyl groups occur as fluorinated groups,
e) fluorosurfactants, which have, in addition to an ionic group, a partially fluorinated alkoxyalkylene group with at least 5 carbon atoms, wherein only ω-mono-, di- or trifluoromethoxy groups or ω-mono-, di-, tri-, tetra- or pentafluoroethoxy groups occur as fluorinated groups,
f) fluorosurfactants, which have, in addition to an ionic group, a partially fluorinated ω-(N,N-diper- or partial fluoromethyl- or ethylamino)alkylene group with at least 7 carbon atoms or a partially fluorinated ω-(N,N-diper- or partial fluoromethyl- or ethylamino)alkyleneoxyalkylene group with at least 7 carbon atoms, wherein only ω-(N,N-diper- or partial fluoromethyl- or ethylamino) groups occur as fluorinated groups,
g) fluorosurfactants, which have, in addition to an ionic group, a partially fluorinated ω-(mono- or diper- or partial fluoromethyl- or ethyl-phenoxy)alkylene group with at least 10 carbon atoms, wherein only ω-(mono- or diper- or partial fluoromethyl or ethylphenoxy) groups occur as fluorinated groups, and
h) fluorosurfactants, which have, in addition to a (poly)alkylene glycol main chain, multiple partially fluorinated or perfluorinated alkoxy groups with fewer than 5 carbon atoms as side chains, as well as also containing at least one nonionic surfactant having silicon-containing groups with a molecular weight of less than 6000 g/mol.

Preferred compositions have a low initial water droplet contact angle of <10° (measured as 50% atmospheric humidity in the climate chamber) 40 seconds after the start of mixing, preferably at any point in time during the processing time between >0 and 3 minutes, and with a droplet age of 10 seconds.

The dynamic course of the water droplet contact angle of the preferred composition, measured 40 seconds after the start of mixing, preferably assumes the following values: after a droplet age of 0.25 second, a water droplet contact angle of <75°, preferably <40°; after a droplet age of 0.5 second, a water droplet contact angle of <55°, preferably <30°; after a water droplet age of 1 second a water droplet contact angle of <35°, preferably <25°; after a droplet age of 2 seconds, a water droplet contact angle of <20°; and after a droplet age of 3 seconds, a water droplet contact angle of <10°.

A water droplet will spread on the uncured inventive composition and will form a droplet having a very small contact angle of <10° after a short period of time, typically after 3 seconds at the latest, or will run completely and form a water film.

The inventive compositions are characterized by the presence of selected nonionic and/or ionic fluorosurfactants which are used in combination with nonionic surfactants having silicon-containing groups.

These combinations are characterized by an especially good wetting behavior.

The fluorosurfactants used according to the invention belong to groups a) through h) defined above.

Fluorosurfactants of group a) contain at least one partially fluorinated or perfluorinated alkylene oxide unit or a partially fluorinated or perfluorinated (poly)alkylene oxide unit (hereinafter referred to as a partially fluorinated or perfluorinated (poly)alkylene oxide unit).

The partially fluorinated or perfluorinated (poly)alkylene oxide unit(s) are preferably linked by a bridge group to a hydrophilic (poly)alkylene oxide unit.

The fluorosurfactants are to be selected as a function of the crosslinkable system. In the organopolysiloxanes that crosslink by means of an addition reaction or the polyethers that contain alkenyl groups and crosslink by means of an addition reaction, fluorosurfactants having sulfur, nitrogen and/or phosphorus atoms intervene in an unfavorable manner in the curing reaction, so it is preferable to exclude fluorosurfactants that contain sulfur, nitrogen and/or phosphorus atoms from these systems.

Fluorosurfactants containing nitrogen, sulfur and/or phosphorus atoms and/or groups containing these atoms may also be used with the other curable systems. Examples include amino groups, sulfonic acid ester groups, phosphoric acid ester groups or phosphonic acid ester groups or carboxylic acid amide groups, sulfonic acid amide groups, phosphoric acid amide groups or phosphonic acid amide groups. Fluorosurfactants having several of these groups and/or atoms, for example, amino groups and carboxylic acid amide groups may also be used as fluorosurfactants.

Nonionic fluorosurfactants of group a) having at least one (poly)alkylene oxide unit and at least one partially fluorinated or perfluorinated (poly)alkylene oxide unit linked together by an oxygen atom or a carboxylic acid ester group are preferred.

Within the scope of this description, partially fluorinated or perfluorinated (poly)alkylene oxide units are understood to be groups having at least one partially fluorinated or perfluorinated alkylene oxide unit, preferably multiple partially fluorinated or perfluorinated alkylene oxide units, wherein the partial fluoroalkylene or perfluoroalkylene groups may have different numbers of carbon atoms in a group. These different partial fluoroalkylene or perfluoroalkylene groups may occur randomly in the group or in the form of blocks of recurring structural units.

Within the scope of this description, (poly)alkylene oxide units are understood to be groups having at least one alkylene oxide unit, preferably multiple alkylene oxide units, wherein the alkylene groups in a group may have different numbers of carbon atoms. These different alkylene groups may occur randomly in the group or in the form of blocks of recurring structural units.

Preferred fluorosurfactants of group a) for use here are block copolymers containing blocks of formula Ia

where $R_F$ is a partially fluorinated or perfluorinated alkylene group with 2 to 12 carbon atoms, wherein the number of carbon atoms of the partially fluorinated or perfluorinated alkylene groups within a polyether group may vary within the scope of the given definitions, $R_H$ denotes an alkylene group with 2 to 12, preferably 2 to 6 carbon atoms, wherein the number of carbon atoms of the alkylene groups may vary within the scope of the given definitions within one polyether group, A' is a covalent bond or a divalent bridge group, which is linked to the blocks [O—$R_F$] and [O—$R_H$] by C—C and/or C—O bonds, a is an integer from 1 to 200, preferably from 1 to 50, in particular from 1 to 20 and d is an integer from 1 to 200, preferably from 1 to 50, in particular from 1 to 10.

The fluorosurfactants of group a) which are especially preferred for use here include the compounds of formula Ib $$R^1—(O—R_F)_a\text{-}A'\text{-}(O—R_H)_b\text{-}A\text{-}(R'_H—O)_c—B \qquad (Ib)$$

where $R^1$ is hydrogen, a partially fluorinated or perfluorinated alkyl group with 1 to 6 carbon atoms or an alkyl group with 1 to 6 carbon atoms, preferably hydrogen, an alkyl group with 1 to 4 carbon atoms or a partially fluorinated or perfluorinated alkyl group with 1 to 4 carbon atoms.

$R_F$ has the meaning defined above, $R_H$ and $R'_H$, independently of one another, denote alkylene groups with 2 to 12 preferably 2 to 6 carbon atoms, wherein the number of carbon atoms of the alkylene groups within a polyether group may vary within the scope of the given definitions, A and A' independently of one another denote a covalent bond or a divalent bridge group, which is linked to the blocks [O—$R_F$], [O—$R_H$] and [$R_H$—O] via C—C and/or C—O bonds, a denotes an integer from 1 to 200, preferably from 2 to 50, b denotes an integer from 0 to 100, preferably from 2 to 50, c denotes an integer from 1 to 100, preferably 2 to 50 and B denotes hydrogen, alkyl, partial fluoroalkyl or perfluoroalkyl.

Compounds of formula Ib are known from EP-B-0 864 643.

Of the nonionic fluorosurfactants of formulas Ia and Ib, the following are especially preferred for use here, namely those in which $R_F$ is a group of formula —$C_{m1}F_{n1}H_{o1}$— or a group of the formula —$CH_2$—$C(CH_3)R^{1a}$—$CH_2$—, wherein the indices m1, n1 and o1 within a polyether group may be different within the scope of the given definitions, m1 is an integer from 2 to 4, n1 is an integer from 1 to 8, o1 is an integer from 0 to 7, wherein the sum of n1 and o1 corresponds to the value 2 m1, $R^{1a}$ is a partially fluorinated or perfluorinated alkyl group with 1 to 4 carbon atoms, $R_H$ is a group of formula —$C_{p1}H_{2p1}$—, wherein the index p1 within a polyether group may be different within the scope of the given definition, $R'_H$ is a group of formula —$C_{q1}H_{2q1}$—, wherein the index q1 may be different within the scope of the given definition in one polyether group, p1 is an integer from 2 to 4, q1 is an integer from 2 to 4, A is a divalent bridge group selected from the group consisting of oxygen atom, carboxylic acid ester or —O—$CH_2$—$CF_2$—, with the provision that the bridge group forms a C—O and/or a C—C bond with the blocks [O—$R_H$] and [$R'_H$—O], A' denotes a covalent bond, a is an integer from 2 to 50, b is an integer from 0 to 25, c is an integer from 1 to 25, d is an integer from 1 to 25 and B denotes hydrogen, alkyl, partial fluoroalkyl or perfluoroalkyl.

Of the nonionic fluorosurfactants of group a), those of formulas Ic or Id are especially preferred

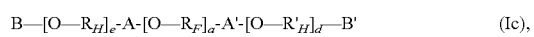

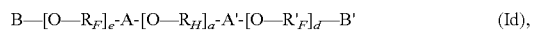

where

A and A' independently of one another denote a covalent bond or divalent bridge group, which is linked to the blocks [O—$R_F$], [O—$R_H$] and [O—$R'_H$] via C—C and/or C—O bonds, B and B' independently of one another denote hydrogen, a partially fluorinated or perfluorinated alkyl group with 1 to 6 carbon atoms or an alkyl group with 1 to 6 carbon atoms, $R_F$ denotes a group of formula —$C_mF_nH_o$—, wherein the indices m, n and o may be different within the scope of the given definitions within one polyether group, $R'_F$ is a group of formula —$C_{m'}F_{n'}H_{o'}$—, wherein the indices m, n and o may be different within the scope of the given definitions within one polyether group, m and m' independently of one another denote integers from 2 to 12, n and n' independently of one another denote integers from 1 to 24, o and o' independently of one another denote integers from 0 to 23, where the sum of n and o corresponds to the value of 2m, $R_H$ is a group of the formula —$C_pH_{2p}$—, wherein the index p may be different within the scope of the given definition in one polyether group, $R'_H$ is a group of formula —$C_qH_{2q}$—, wherein the index q may be different within the scope of the given definition in one polyether group, p is an integer from 2 to 12, preferably from 2 to 4, q is an integer from 2 to 12, preferably from 2 to 4, a is an integer from 1 to 100, preferably 2 to 50, d is an integer from 1 to 100, preferably 2 to 50 and e is an integer from 1 to 100, preferably 2 to 50.

Compounds of formula Ic are known from U.S. Pat. No. 7,230,140 B2.

Groups or A or A' in the compounds of formula Ia, Ib, Ic and Id are preferably covalent bonds or divalent bridge groups selected from the group consisting of oxygen atom, carboxylic acid groups or —O—CH$_2$—CF$_2$—. In the selection of the respective bridge groups, it should be noted that they form C—C and/or C—O bonds with the corresponding blocks.

Most especially preferred are nonionic fluorosurfactants of group a) with formula Ica

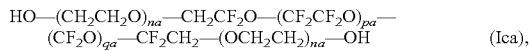

HO—(CH$_2$CH$_2$O)$_{na}$—CH$_2$CF$_2$O—(CF$_2$CF$_2$O)$_{pa}$—(CF$_2$O)$_{qa}$—CF$_2$CH$_2$—(OCH$_2$CH$_2$)$_{na}$—OH  (Ica), where na is an integer from 1 to 20,
pa is an integer from 0 to 12 and
qa is an integer from 0 to 20,
with the provision that the sum of pa and qa must be at least 1.

Nonionic surfactants of this type are available commercially under the brand name Fluorolink® D10-H (Solvay Solexis).

Also preferred are nonionic fluorosurfactants of group a) with the formula Iaa

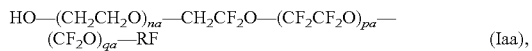

HO—(CH$_2$CH$_2$O)$_{na}$—CH$_2$CF$_2$O—(CF$_2$CF$_2$O)$_{pa}$—(CF$_2$O)$_{qa}$—RF  (Iaa), where the group R$_F$ is a partially fluorinated or perfluorinated alkyl group with 2 to 12 carbon atoms, wherein the number of carbon atoms of the partially fluorinated or perfluorinated alkyl groups within a polyether group may vary within the scope of the given definitions, and the indices na, pa and qa correspond to the explanations of structure Ica.

The fluorosurfactants of group b) are typically compounds of formula Ie

R$^{100}$-IG  (Ie)

where R$^{100}$ is a partially fluorinated or perfluorinated alkyl group with fewer than 5 carbon atoms, and
IG is an ionic group.

Examples of preferred groups IG include carboxylate, sulfonate, sulfate, phosphate, phosphonate or ammonium groups or salts derived from these groups. Examples of salts of carboxylate, sulfonate, sulfate, phosphate and phosphonate groups include the alkaline earth salts, ammonium salts and in particular the alkali salts. Examples of salts of ammonium groups include halides or hydroxides.

Examples of groups R$^{100}$ include partial fluoromethyl or perfluoromethyl, partial fluoroethyl or perfluoroethyl, partial fluoropropyl or perfluoropropyl and partial fluorobutyl or perfluorobutyl. These groups may be linear or branched. Partial fluoropropyl or perfluoropropyl or perfluorobutyl groups are preferred.

The fluorosurfactants of group c) are typically compounds of formula If

R$^{101}$-IG  (If)

where R$^{101}$ is a partially fluorinated or perfluorinated alkoxyalkylene group with fewer than 5 carbon atoms, and
IG is an ionic group, preferably a carboxylate, sulfonate, sulfate, phosphate, phosphonate or ammonium group or a salt derived from one of these groups.

Examples of groups R$^{101}$ include partial fluoromethoxymethylene or perfluoromethoxymethylene, partial fluoromethoxyethylene or perfluoromethoxyethylene, partial fluoromethoxypropylene or perfluoromethoxypropylene, partial fluoroethoxymethylene or perfluoroethoxymethylene, partial fluoroethoxyethylene or perfluoroethoxyethylene, partial fluoropropoxymethylene or perfluoropropoxymethylene. These groups may be linear or branched.

The fluorosurfactants of group d) are typically compounds of formula Ig

R$^{102}$-R$^{103}$-IG  (Ig)

where R$^{102}$ is a partial fluoromethyl or perfluoromethyl or ethyl group,
R$^{103}$ is an alkylene group with at least 3 carbon atoms, where the sum of the carbons of R$^{102}$ and R$^{103}$ is at least 5, and
IG is an ionic group, preferably a carboxylate, sulfonate, sulfate, phosphate, phosphonate or ammonium group or a salt derived from one of these groups.

Examples of groups R$^{102}$ include mono-, di- or trifluoromethyl or mono-, di-, tri-, tetra- or pentafluoroethyl. These groups may be linear or branched.

Examples of groups R$^{103}$ include propylene, butylenes, pentylene, hexylene, heptylene, octylene, nonylene or decylene. These groups may also be linear or branched.

The fluorosurfactants of group e) are typically compounds of formula Ih

R$^{104}$—R$^{103}$-IG  (Ih)

where R$^{104}$ is a partial fluoromethoxy or perfluoromethoxy or ethoxy group,
R$^{103}$ has the meaning defined above, where the sum of the carbons of R$^{104}$ and R$^{103}$ is at least 5, and
IG is an ionic group, preferably a carboxylate, sulfonate, sulfate, phosphate, phosphonate or ammonium group or a salt derived from one of these groups.

Examples of groups R$^{104}$ include mono-, di- or trifluoromethoxy or mono-, di-, tri-, tetra- or pentafluoroethoxy. These groups may be linear or branched.

Examples of group R$^{103}$ are given above.

The fluorosurfactants of group f) are typically compounds of formula Ii

where R$^{105}$ and R$^{106}$ independently of one another denote partial fluoromethyl or perfluoromethyl or ethyl groups,
R$^{103}$ has the meaning defined above, where the sum of carbons of R$^{105}$, R$^{106}$ and R$^{103}$ is at least 7, and
IG is an ionic group, preferably a carboxylate, sulfonate, sulfate, phosphate, phosphonate or ammonium group or a salt derived from one of these groups.

Examples of groups R$^{105}$ and R$^{106}$ include mono-, di- or trifluoromethyl or mono-, di-, tri-, tetra- or pentafluoroethyl. These groups may be linear or branched.

Examples of group R$^{103}$ are explained above.

The fluorosurfactants of group g) are typically compounds of formula Ij

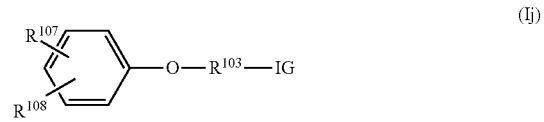

where R$^{107}$ and R$^{108}$ independently of one another denote hydrogen or partial fluoromethyl or perfluoromethyl or ethyl groups, where at least one of these groups is a partial fluoromethyl or perfluoromethyl or ethyl group,
$R^{103}$ has the meaning defined above, where the sum of the carbons of $R^{107}$, $R^{108}$, $R^{103}$ and phenyl is at least 10, and
IG is an ionic group, preferably a carboxylate, sulfonate, sulfate, phosphate, phosphonate or ammonium group or a salt derived from one of these groups.

Examples of groups $R^{107}$ and $R^{108}$ include mono-, di- or trifluoromethyl or mono-, di-, tri-, tetra- or pentafluoroethyl. These groups may be linear or branched.

Examples of group $R^{103}$ are explained above.

The fluorosurfactants of group h) are typically compounds with structural units of formula Ik and/or Il

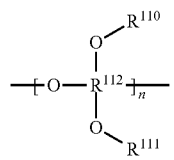
(Il)

-continued

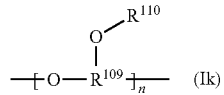
(Ik)

where $R^{109}$ is a trivalent aliphatic hydrocarbon group,
$R^{110}$ and $R^{111}$ independently of one another denote partial fluoroalkyl or perfluoroalkyl groups with 1 to 4 carbon atoms,
$R^{112}$ is a tetravalent aliphatic hydrocarbon group and
n is an integer of at least 1, preferably 1 to 20.

Examples of groups $R^{109}$ are groups derived from trimethylolpropane.

Examples of groups $R^{112}$ are groups derived from pentaerythritol.

Examples of groups $R^{110}$ and $R^{111}$ are mono-, di- or trifluoromethyl, mono-, di-, tri-, tetra- or pentafluoroethyl, mono-, di-, tri-, tetra-, penta-, hexa- or hepta-fluoropropyl, or mono-, di-, tri-, tetra-, penta-, hexa-, hepta-, octa- or nonafluoro-butyl. These groups may be linear or branched.

In addition to the structural units of formula Ik and/or Il, fluorosurfactants of group h) preferably contain structural units of formula Im

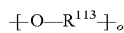
(Im)

where $R^{113}$ denotes an alkylene group with at least 2 carbon atoms, and o is an integer of at least 1, preferably 2 to 50.

Especially preferred fluorosurfactants used according to the invention have very good biodegradability and have acceptable findings according to ISO 10993-1 for use in dental impression compounds or have none at all.

In a preferred embodiment, the fluorosurfactants of groups a) through h) are used in combination with other ionic and/or nonionic and/or amphoteric fluorosurfactants.

Combinations of fluorosurfactants of groups a) through h) with additional nonionic surfactants are especially preferred for use here.

The nonionic surfactants that are especially preferred for use here include fatty alcohol ethoxylates in particular compounds of general formula $R^{114}$—O—$(CH_2—CH_2—O)_{n10}$—$R^{115}$, where $R^{114}$ denotes alkyl, in particular $C_{10}$-$C_{18}$ alkyl, $R^{115}$ denotes hydrogen or an alkyl with up to 4 carbon atoms, and n10 is an integer from 1 to 30, or
alkylphenylethoxylates, in particular compounds of the general formula $R^{116}$—$C_6H_4$—O—$(CH_2—CH_2—O)_{n11}$—$R^{117}$, where $R^{116}$ denotes alkyl, in particular $C_6$-$C_{12}$ alkyl, $R^{117}$ denotes hydrogen or alkyl with up to 4 carbon atoms, and n11 is an integer from 1 to 30 or
polysorbates, in particular compounds of formula In

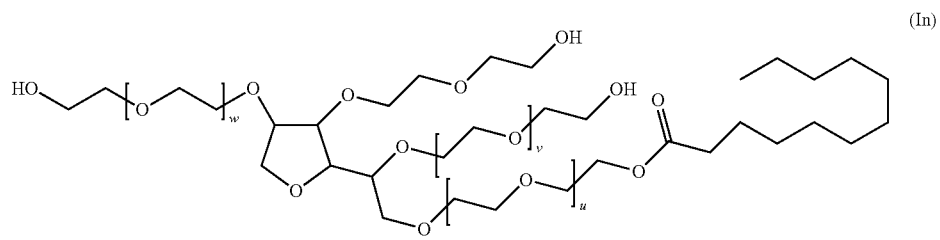
(In)

where u, v and w, independently of one another, are integers from 2 to 20 or alkylpolyglucosides, in particular compounds of formula Io

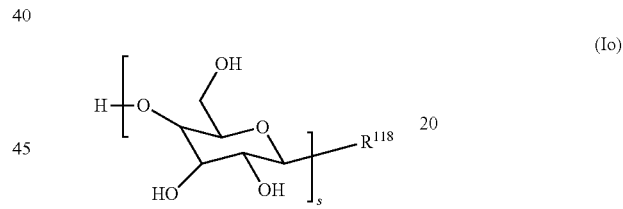
(Io)

where $R^{118}$ is a long-chain alkyl, in particular a $C_6$-$C_{16}$ alkyl, and s is an integer from 1 to 10.

Combinations of fluorosurfactants of groups a) through h) with additional anionic surfactants are also especially preferred for use here.

The anionic surfactants that are especially preferred here include alkyl or alkenyl carboxylates or the salts thereof, in particular compounds of the general formula $(R^{119}$—$COO^-)_tM^{t+}$, where $R^{119}$ denotes long-chain alkyl or long-chain alkenyl, in particular $C_6$-$C_{18}$ alkyl or $C_6$-$C_{18}$ alkenyl, M is hydrogen or a t-valent metal ion, and t is 1, 2 or 3; or
alkylbenzenesulfonates, in particular compounds of the general formula $(R^{120}$—$C_6H_4$—$SO_3^-)_tM^{t+}$, where $R^{120}$ denotes alkyl, in particular $C_4$-$C_{18}$ alkyl, M is hydrogen or a t-valent metal ion, and t is 1, 2 or 3; or
alkylsulfonates, in particular compounds of the general formula $(R^{121}$—$SO_3^-)_tM^{t+}$, where $R^{121}$ denotes alkyl, in particular $C_4$-$C_{18}$ alkyl, M is hydrogen or a t-valent metal ion, and t is 1, 2 or 3; or fatty alcohol sulfonates in particular compounds of the general formula $(R^{121}—OSO_3^-)_tM^{t+}$, where $R^{121}$ denotes alkyl, in particular $C_4$-$C_{18}$ alkyl, M is hydrogen or a t-valent metal ion and t is 1, 2 or 3; or dialkylsulfosuccinates, in particular compounds of the general formula $(R^{122}—O—CO—CH_2—CH(SO_3^-)—CO—O—R^{123})_tM^{t+}$, where $R^{122}$ and $R^{123}$, independently of one another, denote alkyl, in particular $C_4$-$C_{18}$ alkyl, M is hydrogen or a t-valent metal ion, and t is 1, 2 or 3.

Combinations of fluorosurfactants of groups a) through h) with additional cationic surfactants are also especially preferred for use here.

The cationic surfactants that are especially preferred for use here include quaternary ammonium compounds, in particular compounds of the general formula $(R^{124}R^{125}R^{126}R^{127}N)_t^+An^{t-}$, where $R^{124}$, $R^{125}$, $R^{126}$ and $R^{127}$, independently of one another, denote hydrogen, alkyl or aryl, at least one of these groups being a long-chain alkyl, in particular $C_6$-$C_{18}$ alkyl, An is a t-valent anion, preferably a halide anion, and t is 1, 2 or 3; or quaternary ammonium ester compounds, in particular compounds of the general formula $(R^{128}R^{129}N(R^{130}—COOR^{131})_2)_t^+An^{t-}$, where $R^{128}$ and $R^{129}$, independently of one another, denote hydrogen, alkyl or aryl, at least one of these groups being a long-chain alkyl, in particular $C_6$-$C_{18}$ alkyl, $R^{130}$ is an alkylene group, in particular an alkylene group with 2 to 4 carbon atoms, $R^{131}$ denotes alkyl or aryl, preferably $C_1$-$C_6$ alkyl, An denotes a t-valent anion, preferably a halide anion, and t is 1, 2 or 3.

Combinations of fluorosurfactants of groups a) through h) with additional amphoteric surfactants are also especially preferably used.

The amphoteric surfactants especially preferred here include betaines, in particular compounds of the general formula $(R^{132}CO—NH—R^{133}—N^+R^{134}R^{135}R^{136}—COO^-)$, where $R^{132}$, $R^{134}$ and $R^{135}$, independently of one another, denote alkyl or aryl, preferably $C_1$-$C_6$ alkyl, $R^{133}$ and $R^{136}$ are alkylene, one of which is optionally substituted with a hydroxyl group, preferably $C_1$-$C_4$ alkylene; or sultaines, in particular compounds of the general formula $(R^{137}CO—NH—R^{138}—N^+R^{139}R^{140}$-$R^{141}—SO_3^-)$, where $R^{137}$, $R^{139}$ and $R^{140}$, independently of one another, denote alkyl or aryl, preferably $C_1$-$C_6$ alkyl, $R^{138}$ and $R^{141}$ are alkylene, one of which is optionally substituted with a hydroxyl group, preferably $C_1$-$C_4$ alkylene.

The silicon-containing surfactant used according to the invention preferably contains at least one (poly)alkylene oxide group and has a molecular weight of less than 6000 g/mol, preferably less than 4000 g/mol, in particular 350 g/mol to 2000 g/mol.

The silicon-containing surfactant used according to the invention has, in addition to the at least one (poly)alkylene oxide group, at least one group which contains organosiloxane groups or organosilane groups. The organic groups are hydrocarbon groups, which are optionally partially fluorinated or perfluorinated.

Such organosiloxane surfactants or organocarbosilane surfactants are known per se.

Silicon-containing surfactants, which are organosiloxane surfactants of formulas II or III, or organocarbosilane surfactants of formulas IV, V or VI are preferred

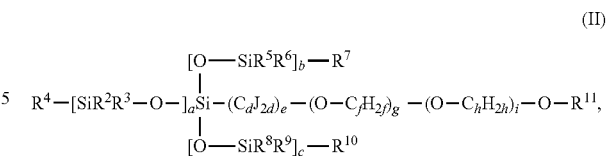

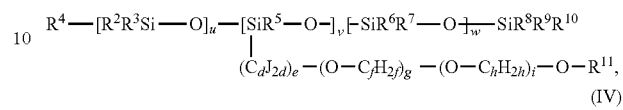

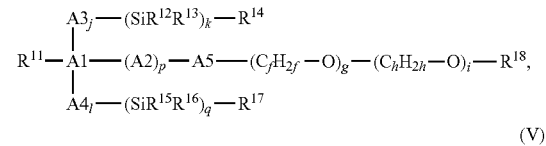

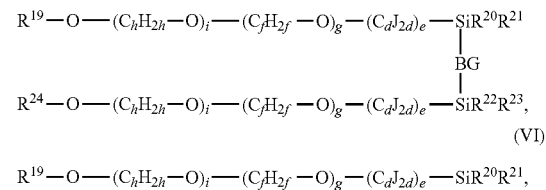

where $R^2$, $R^3$, $R^4$, $R^5$, $R^6$, $R^7$, $R^8$, $R^9$ and $R^{10}$ independently of one another denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are optionally partially or completely fluorinated, preferably alkyl or alkenyl and especially $C_1$-$C_6$ alkyl, a, b, c and w, independently of one another, are integers from 0 to 100, preferably 0 to 75, in particular 0 to 35, and most especially preferably 0 to 15, v is an integer from 1 to 100, preferably 1 to 15, and most especially preferably 1 to 6, where the sum of a, b and c is between 1 and 300, preferably 1 to 50, especially 1 to 10 and most especially preferably 1 to 3, and the sum of v and w is between 1 and 200, preferably 2 to 90, u is 0 or 1, d is an integer from 1 to 10, preferably 1 to 6 and especially 1 to 3, J is hydrogen or fluorine, preferably hydrogen, e is 0 or 1, f and h, independently of one another, are integers from 2 to 6, g and i independently of one another are integers from 0 to 30, preferably 0 to 15, where the sum of g and i is 1 to 60, preferably 2 to 30, especially 2 to 15, $R^{11}$ is hydrogen, alkyl, alkenyl or aryl, optionally partially or completely fluorinated, preferably hydrogen or methyl, $R^{12}$, $R^{13}$, $R^{14}$, $R^{15}$, $R^{16}$ and $R^{17}$ independently of one another denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are optionally partially or completely fluorinated, preferably alkyl or alkenyl and especially $C_1$-$C_6$ alkyl, k and q independently of one another are 0 or 1, A1 is carbon or silicon, A2, A3 and A4 independently of one another are a group $C_dJ_{2d}$, where J and d have the meanings defined above, j, p and l independently of one another are 0 or 1, A5 is a divalent bridge group, especially —O—, —CO—O— or —CO—, $R^{18}$ is hydrogen, alkyl, alkenyl or aryl, optionally partially or completely fluorinated, preferably hydrogen or methyl, $R^{20}$, $R^{21}$, $R^{22}$ and $R^{23}$ independently of one another denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, optionally partially or completely fluorinated, preferably alkyl or alkenyl and especially $C_1$-$C_6$ alkyl, BG is a divalent bridge group, and $R^{19}$ and $R^{24}$ independently of one another denote hydrogen, alkyl, alkenyl or aryl, which are optionally partially or completely fluorinated, preferably hydrogen or methyl, with the provision that of the groups $R^2$, $R^3$ and $R^4$ and/or the groups $R^5$, $R^6$ and $R^7$ and/or the groups $R^8$, $R^9$ and $R^{10}$ and/or the groups $R^{15}$, $R^{16}$ and $R^{17}$ and/or the groups $R^{20}$ and $R^{21}$ and/or the groups $R^{22}$ and $R^{23}$ and/or the groups $R^{20}$, $R^{21}$ and $R^{22}$, only one can be hydrogen, where f and h may assume different values within one molecule within the scope of the given definition.

Different indices f and h mean that alkylene oxide units of different carbon numbers may be present and may occur in random distribution or in the form of blocks.

Organosiloxane surfactants of formula IIIa are especially preferably used

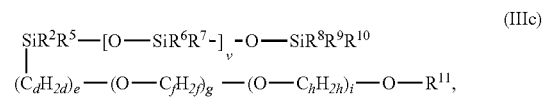
(IIIa)

where $R^2$, $R^3$, $R^4$, $R^5$, $R^6$, $R^7$, $R^8$, $R^9$ and $R^{10}$, independently of one another, denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, preferably hydrogen, alkyl, alkyloxy or alkenyl, v is an integer from 1 to 100, w is an integer from 0 to 100, d is an integer from 1 to 10, e is 0 or 1, f and h, independently of one another, denote integers from 2 to 6, g and i, independently of one another, denote integers from 0 to 30, where the sum of g and i is 1 to 60, and $R^{11}$ is hydrogen, alkyl, alkenyl or aryl.

Other especially preferred organosiloxane surfactants are compounds of formulas IIIb or IIIc

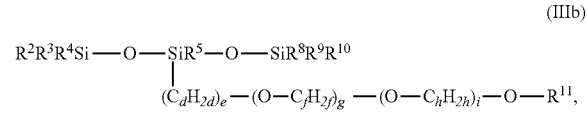
(IIIb)

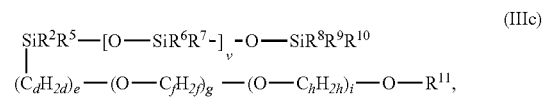
(IIIc)

where $R^2$, $R^3$, $R^4$, $R^5$, $R^6$, $R^7$, $R^8$, $R^9$ and $R^{10}$, independently of one another, denote hydrogen, alkyl or alkenyl, preferably hydrogen, methyl especially butyloxy and methoxy, vinyl or allyl, v is an integer from 1 to 100, d, e, f, g, h and i have the meanings defined above and $R^{11}$ is hydrogen, alkyl, alkenyl or aryl.

Most especially preferred organosiloxane surfactants are compounds of formula IIId

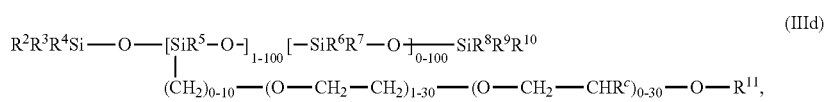
(IIId)

where $R^2$, $R^3$, $R^4$, $R^5$, $R^6$, $R^7$, $R^8$, $R^9$ and $R^{10}$, independently of one another, denote alkyl, alkenyl, alkynyl, aryl, aryloxy, aralkyl, aralkyloxy, alkylaryl or alkylaryloxy preferably methyl, $R^c$ denotes $C_1$-$C_6$ alkyl, preferably methyl or ethyl or phenyl and $R^{11}$ is hydrogen, alkyl, alkenyl or aryl, preferably hydrogen or methyl.

Other most especially preferred organosiloxane surfactants are compounds of formula IIIe

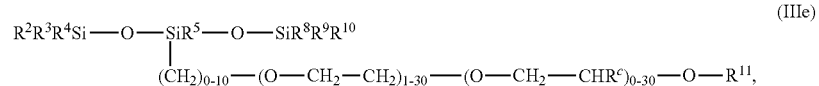
(IIIe)

where $R^2$, $R^3$, $R^4$, $R^5$, $R^8$, $R^9$ and $R^{10}$, independently of one another, denote alkyl, alkenyl, alkynyl, aryl, aryloxy, aralkyl, aralkyloxy, alkylaryl or alkylaryloxy, preferably methyl, $R^c$ is $C_1$-$C_6$ alkyl preferably methyl or ethyl or phenyl and $R^{11}$ is hydrogen, alkyl, alkenyl or aryl, preferably hydrogen or methyl.

Other most especially preferred organosiloxane surfactants are compounds of formula IIIf

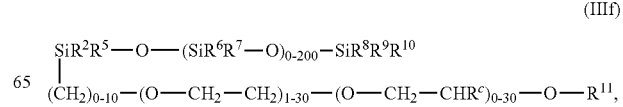
(IIIf)

where $R^2$, $R^5$, $R^6$, $R^7$, $R^8$, $R^9$ and $R^{10}$, independently of one another, denote alkyl, alkenyl, alkynyl, aryl, aralkyl or alkylaryl preferably methyl,
$R^c$ is $C_1$-$C_6$ alkyl preferably methyl or ethyl or phenyl and
$R^{11}$ is hydrogen, alkyl, alkenyl or aryl, preferably hydrogen or methyl.

Most especially preferred are organosiloxane surfactants of formula IIIg

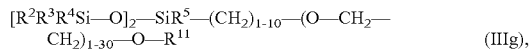
(IIIg), where $R^2$, $R^3$, $R^4$ and $R^5$, independently of one another, denote alkyl and/or alkenyl, preferably methyl,
$R^{11}$ is hydrogen, alkyl, alkenyl or aryl, preferably hydrogen or methyl.

Most especially preferred silicon-containing surfactants are compounds of formulas VII, VIII, IX and X

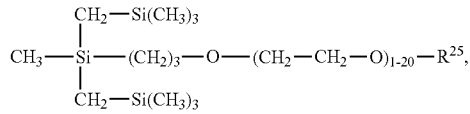
(VII)

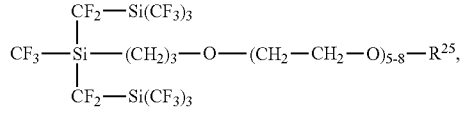
(VIII)

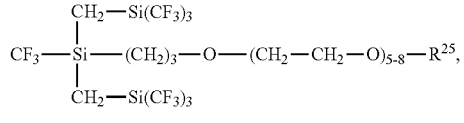
(IX)

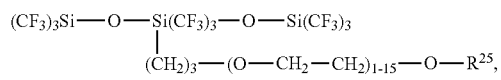
(X)

where $R^{25}$ is hydrogen, methyl, ethyl, propyl or butyl, preferably hydrogen or methyl.

These preferred silicone surfactants or carbosilane surfactants are available commercially, for example, under the brand name Masil SF 19 (Lubrizol), Silwet L77 (GE-Bayer Silicones).

Carbosilane surfactants of formula Iva are especially preferred for use here

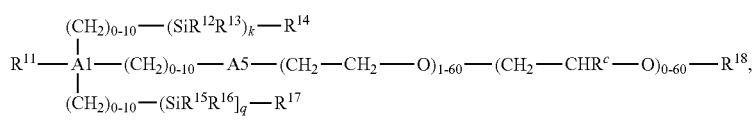
(IVa)

where $R^{11}$, $R^{12}$, $R^{13}$, $R^{14}$, $R^{15}$, $R^{16}$ and $R^{17}$, independently of one another, denote hydrogen, alkyl, alkenyl, alkynyl, aryl, aralkyl or alkylaryl,
the sum of k and q is 1 or 2,
A5 is a group —O—, —CO—, —CO—O—, —S—, —NR$^{19}$—, —CO—NR$^{19}$—, —SO$_2$— or —SO$_2$—NR$^{19}$—,
$R^{19}$ is hydrogen, alkyl, alkenyl or aryl,
$R^c$ is $C_1$-$C_6$ alkyl preferably methyl or ethyl or phenyl and
$R^{18}$ is hydrogen, alkyl, alkenyl or aryl.

Carbosilane surfactants of formula Va are also especially preferably used here

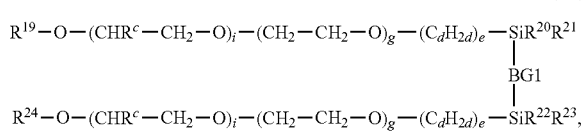
(Va)

where $R^{20}$, $R^{21}$, $R^{22}$ and $R^{23}$, independently of one another, denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, preferably hydrogen, alkyl, alkyloxy or alkenyl,
d is an integer from 1 to 10,
e is 0 or 1,
g and i independently of one another are integers from 0 to 30, where the sum of g and i is 1 to 60,
BG1 is a bridge group selected from the groups of formulas —O—, alkylene, polyoxyalkylene, phenylene, cycloalkylene, bicycloalkadiendiyl and —C$_6$H$_5$—K—C$_6$H$_5$—,
K is a direct C—C bond, —O—, —SO$_2$—, alkylene or haloalkylene and
$R^{19}$ and $R^{24}$ independently of one another denote hydrogen, alkyl, alkenyl or aryl.

Compounds of formula Va are most especially preferred, where BG1 is a bridge group selected from the group consisting of formulas —O—, $C_1$-$C_{10}$ alkylene, —(O—CH$_2$—CHR$^c$)$_{2-60}$—, —(CF$_{12}$)$_{1-10}$—(O—CH$_2$—CHR$^c$)$_{2-60}$—(CH$_2$)$_{1-10}$—, phenylene, cyclohexylene, cyclopentylene, norbonene-diyl, bis-cyclopentadienyl-diyl, —C$_6$H$_5$—O—C$_6$H$_5$—, —C$_6$H$_5$—SO$_2$—C$_6$H$_5$—, —C$_6$H$_5$—C(CH$_3$)$_2$—C$_6$H$_5$— and —C$_6$H$_5$—C(CF$_3$)$_2$—C$_6$H$_5$—.

Carbosilane surfactants of formula VIa are also especially preferred for use here

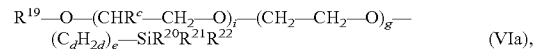
(VIa), where $R^{20}$, $R^{21}$ and $R^{22}$ independently of one another denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, preferably hydrogen, alkyl, alkyloxy or alkenyl,
d is an integer from 1 to 10,
e is 0 or 1,
g and i independently of one another are integers from 0 to 30, where the sum of g and i is 1 to 60 and
$R^{19}$ and $R^{24}$ independently of one another denote hydrogen, alkyl, alkenyl or aryl.

Fluorocarbosilane surfactants of formula IVb are especially preferred for use here

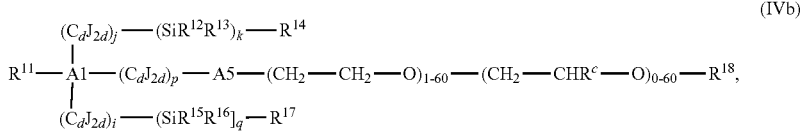

(IVb)

where $R^{11}$, $R^{12}$, $R^{13}$, $R^{14}$, $R^{15}$, $R^{16}$ and $R^{17}$ independently of one another denote hydrogen, fluoro, alkyl, alkyloxy, alkenyl, alkenyloxy, alkynyl, alkynyloxy, aryl, aryloxy, aralkyl, alkylaryl, fluoroalkyl, fluoroalkyloxy, fluoroalkenyl, fluoroalkenyloxy, fluoroalkynyl, fluoroalkynyloxy, fluoroaryl, fluoroaryloxy, fluoroaralkyl or fluoroalkylaryl, preferably hydrogen, fluoro, alkyl, fluoroalkyl, alkoxy, fluoroalkoxy, alkenyl and fluoroalkenyl, where at least one of these groups contains fluorine and the fluorine-containing groups may be partially fluorinated or perfluorinated,
d is an integer from 1 to 10,
j, p and l are 0 or 1,
the sum of k and q is 1 or 2,
A5 is a group —O—, —CO—O—, —S—, —NR$^{19}$—, —CO—NR$^{19}$—, —SO$_2$— or —SO$_2$—NR$^{19}$—,
$R^{19}$ is hydrogen, alkyl, alkenyl or aryl,
$R^c$ is $C_1$-$C_6$ alkyl, preferably methyl or ethyl or phenyl and
$R^{18}$ is hydrogen, alkyl, alkenyl or aryl.

Fluorosilicone surfactants of formula IVc are most especially preferred for use here

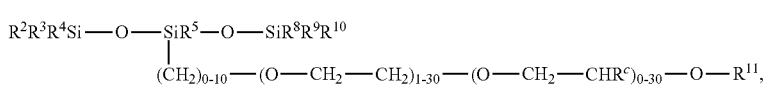

(IVc)

where $R^2$, $R^3$, $R^4$, $R^5$, $R^8$, $R^9$ and $R^{10}$ independently of one another denote alkyl, alkyloxy, alkenyl, alkenyloxy, alkynyl, alkynyloxy, aryl, aryloxy, aralkyl, aralkyloxy, alkylaryl or alkylaryloxy, fluoroalkyl, fluoroalkyloxy, fluoroalkenyl, fluoroalkenyloxy, fluoroalkynyl, fluoroalkynyloxy, fluoroaryl, fluoroaryloxy, fluoroaralkyl, fluoroaralkyloxy, fluoroalkylaryl or fluoroalkylaryloxy, preferably methyl, trifluoromethyl, $C_1$-$C_4$ alkoxy, $C_1$-$C_4$-fluoroalkoxy especially methoxy or trifluoromethyl, and/or vinyl and/or allyl, where at least one of these groups contains fluorine and the fluorine-containing groups may be partially fluorinated or perfluorinated,
$R^c$ denotes $C_1$-$C_6$ alkyl preferably methyl or ethyl or phenyl and
$R^{11}$ denotes hydrogen, alkyl, alkenyl or aryl, preferably hydrogen or methyl.

Fluorocarbosilane surfactants of formula Vc are also especially preferably preferred for use here

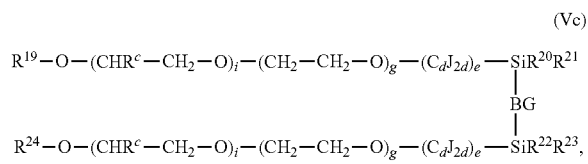

(Vc)

where $R^{20}$, $R^{21}$, $R^{22}$ and $R^{23}$ independently of one another denote hydrogen, fluoro, alkyl, alkyloxy, alkenyl, alkenyloxy, alkynyl, alkynyloxy, aryl, aryloxy, aralkyl, aralkyloxy, alkylaryl and/or alkylaryloxy, fluoroalkyl, fluoroalkyloxy, fluoroalkenyl, fluoroalkenyloxy, fluoroalkynyl, fluoroalkynyloxy, fluoroaryl, fluoroaryloxy, fluoroaralkyl, fluoroaralkyloxy, fluoroalkylaryl and/or fluoroalkylaryloxy, preferably hydrogen, fluoro, alkyl, fluoroalkyl, alkyloxy, fluoroalkyloxy, alkenyl or fluoroalkenyl, where at least one of these groups contains fluorine and the fluorine-containing groups may be partially fluorinated or perfluorinated,
d is an integer from 1 to 10,
e is 0 or 1,
g and i independently of one another denote integers from 0 to 30 where the sum of g and i is 1 to 60,
BG is a bridge group selected from the groups of formulas —O—, alkylene, polyoxyalkylene, phenylene, cycloalkylene, bicycloalkadiendiyl and —C$_6$H$_5$—K—C$_6$H$_5$—,
K is a direct C—C bond, —O—, —SO$_2$—, alkylene or haloalkylene, and
$R^{19}$ and $R^{24}$, independently of one another, denote hydrogen, alkyl, alkenyl or aryl.

The most especially preferred compounds of formula Vc are those in which BG is a bridge group selected from the group consisting of formulas —O—, $C_1$-$C_{10}$ alkylene, —(O—CH$_2$—CHR$^c$)$_{2\text{-}60}$—, —(CH$_2$)$_{1\text{-}10}$-(O—CH$_2$—CHR$^c$)$_{2\text{-}60}$—(CH$_2$)$_{1\text{-}10}$—, phenylene, cyclohexylene, cyclopentylene, norbonene-diyl, bis-cyclopentadienyl-diyl, —C$_6$H$_5$—O—C$_6$H$_5$—, —C$_6$H$_5$—SO$_2$—C$_6$H$_5$—, —C$_6$H$_5$—C(CH$_3$)$_2$—C$_6$H$_5$— and —C$_6$H$_5$—C(CF$_3$)$_2$—C$_6$H$_5$—.

Fluorocarbosilane surfactants of formula VIb are also especially preferred

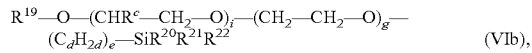

(VIb), where $R^{20}$, $R^{21}$ and $R^{22}$ independently of one another denote hydrogen, fluoro, alkyl, alkenyl, alkynyl, aryl, aralkyl and/or alkylaryl, fluoroalkyl, fluoroalkenyl, fluoroalkynyl, fluoroaryl, fluoroaralkyl and/or fluoroalkylaryl, preferably hydrogen, fluoro, alkyl, fluoroalkyl, alkenyl or fluoroalkenyl, where at least one of these groups contains fluorine and the fluorine-containing groups may be partially fluorinated or perfluorinated,
d is an integer from 1 to 10,
e is 0 or 1,
g and i, independently of one another, are integers from 0 to 30, where the sum of g and i is 1 to 60, and
$R^{19}$ and $R^{24}$ independently of one another denote hydrogen, alkyl, alkenyl or aryl.

The nonionic silicone surfactants or nonionic carbosilane surfactants of formulas II to X are used individually or in combination with the fluorosurfactants of groups a) through h), in particular with those of formulas Ia through Il, or together with mixtures of two or more of these fluorosurfactants.

The amount of fluorosurfactant of groups a) through h) in the inventive composition is usually 0.001 to 5.0 wt %, preferably 0.01 to 5.0 wt %. based on the composition.

If other nonionic, anionic, cationic and/or amphoteric fluorosurfactants are used in the inventive composition in addition to the fluorosurfactant of groups a) through h), then the amount thereof in the inventive composition will usually also be 0.001 to 5.0 wt %, preferably 0.01 to 5.0 wt %, based on the composition.

The amount of silicon-containing nonionic surfactant in the inventive composition is usually 0.0 to 5.0 wt %, preferably 0.05 to 5.0 wt %, especially preferably 0.1 to 5.0 wt %, based on the composition.

If combinations of fluorosurfactant of groups a) through h) with another fluorosurfactant are used in the inventive compositions, then the weight ratio of fluorosurfactants of groups a) through h) to other fluorosurfactants is 100:1 to 1:100, preferably 50:1 to 1:50, especially preferably 10:1 to 1:10 and especially preferably 4:1 to 1:5.

In the inventive combinations of fluorosurfactant with silicone surfactant, the weight ratio of silicon-containing nonionic surfactant to nonionic fluorosurfactant is 100:1 to 1:100, preferably 50:1 to 1:50, especially preferably 10:1 to 1:10 and especially preferably 4:1 to 1:5.

The inventive composition preferably contain, in addition to the fluorosurfactant of groups a) through h), the silicone surfactant and optionally other fluorosurfactant, as an additional component an alkenyl group and/or alkynyl group-containing polyether and/or a hydroxyl- and/or aryloxy- and/or arylalkyloxy- and/or alkoxy-terminated polyether.

This additional component causes a further improvement in the contact angle properties of the uncured plastic material and thus a further improvement in the fidelity of the resulting impression, Examples of preferred additives of this type include compounds of formula XI $$R^{30}\text{-A-}(R^{30})_{n1} \quad (XI),$$

where $R^{30}$ is an ethylenically unsaturated hydrocarbon group, preferably allyl, styryl, acryloyl or methacryloly or hydrogen or alkyl, and several groups $R^{30}$ of a molecule may be different within the scope of the given definition, n1 is an integer from 1 to 5, preferably 1, 2 or 3, especially 1, A is a group of the formula $Z\text{—}(O\text{—}(C_{n2}H_{2n2}\text{—}O)_{m1}\text{—})_{n1+1}$, Z is an n1-valent hydrocarbon group, preferably a group derived from a divalent, trivalent, tetravalent, pentavalent or hexavalent aliphatic alcohol, especially a group derived from alkylene glycol, trimethylol propane, pentaerythritol or sorbitol, n2 is an integer from 2 to 8, preferably 2 to 4 and
m1 is an integer from 1 to 35,000, preferably from 50 to 1500, where n2 and m1 may be different within one molecule within the scope of the given definition.

The indices n2 and/or m1 may assume different values within one molecule and within one alkylene oxide chain within the scope of the given definition. Different indices n2 and/or m1 mean that alkylene oxide units of different carbon numbers may be present, which may occur in random distribution or in the form of blocks and/or the individual blocks may have different lengths within one molecule.

Polyethers that are most especially preferred for use here include compounds of formulas XII and XIII

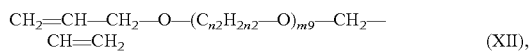

$$CH_2\!=\!CH\!-\!CH_2\!-\!O\!-\!(C_{n2}H_{2n2}\!-\!O)_{m9}\!-\!CH_2\!-\!CH\!=\!CH_2 \quad (XII),$$

$$R^{31}\!-\!O\!-\!(C_{n2}H_{2n2}\!-\!O)_{m9}\!-\!R^{32} \quad (XIII),$$

where n2 denotes an integer from 2 to 8, preferably from 2 to 4,
m9 is an integer from 3 to 70,000, preferably from 10 to 2500, where n2 and m9 may be different within one molecule within the scope of the given definition and $R^{31}$ and $R^{32}$ independently of one another denote hydrogen or $C_1$-$C_6$ alkyl, especially hydrogen and/or methyl, ethyl or propyl.

Examples of especially preferred alkylene oxide units  —$CH_2$—$CH_2$—O—, —$CH_2$—$CH_2$—$CH_2$—O—, —$CH_2$—$CH(CH_3)$—O— and —$CH_2$—$CH_2$—$CH_2$—$CH_2$—O—.

Polyethers of formulas XII and XIII, especially those having ethylene oxide units or ethylene oxide units and propylene oxide units or ethylene oxide units and butylenes oxide units are especially preferred.

These polyethers are generally used as mixtures of polymers of different chain lengths. Typical molecular weights (number average) vary in the range from 150 to 3,000,000, preferably 250 to 100,000 and especially preferably from 250 to 50,000.

The amount of these polyethers in the inventive composition is usually 0.1 to 25.0 wt %, preferably 0.1 to 10.0 wt % and especially preferably 0.5 to 2.5 wt %, based on the composition.

The inventive compositions preferably contain a polyol as an additional component, in addition to the fluorosurfactant of groups a) through h), the silicone surfactant, and optionally another fluorosurfactant.

This additional component causes a further improvement in the contact angle properties of the uncured plastic material and thus a further improvement in the precision of detail of the resulting impression.

This additional component may be monomeric, oligomeric or polymeric polyols which may have primary, secondary and/or tertiary hydroxyl groups. The hydroxyl groups may be bound to aromatic groups but preferably to aliphatic groups.

The amount of these polyols in the inventive composition is usually 0.1 to 25.0 wt %, preferably 0.1 to 10.0 wt % and especially preferably 0.5 to 2.5 wt %, based on the composition.

Preferred polyols are selected from the group of carbohydrates, polyvinyl alcohols, aliphatic di-, tri-, tetra-, penta- and/or hexaols and mixtures of two or more of these polyols.

Especially preferred polyols are selected from the group of polyvinyl alcohols, polysaccharides, trimethylolpropane, pentaerythritol, dipentaerythritol, glycerol, allyloxy-1,2-propanediol, 2-methyl-2,4-pentanediol, trimethylol propane allyl ether, decanediol, nonanediol, octanediol, heptanediol, hexanediol, pentanediol, butanediol, propanediol, ethanediol, fructose, glucose and mixtures of two or more of these polyols, especially glycerol.

In another preferred embodiment, the inventive composition contains, in addition to the polyol, an alkenyl group and/or alkynyl group-containing polyether and/or an aryloxy- and/or arylalkyloxy- and/or hydroxyl- and/or alkoxy-terminated polyether as the additional component.

Due to the presence of these two components, the contact angle properties of the uncured plastic material can be improved.

Different types of curable polymer systems may be used. Depending on the respective polymer system, the inventive compositions may be in the form of single component systems or multicomponent systems, preferably as two component systems. Those skilled in the art will be readily familiar with the curable polymer systems and their additional components, such as catalysts and/or initiators.

The amount of curable polymers in the inventive composition is usually 5 to 80 wt %, preferably 20 to 70 wt %, based on the composition.

The amount of catalyst and/or photoinitiators in the inventive composition is usually 0.00005 to 10 wt %, preferably 0.0001 to 5 wt %, based on the composition.

Compositions containing a crosslinkable polyether having alkoxysilyl groups, aziridino groups, groups derived from an ethylenically unsaturated carboxylic acid, alkenyl groups as crosslinkable groups or groups crosslinkable via a ring-opening metathesis reaction, a crosslinking catalyst and/or a photoinitiator as well as a fluorosurfactant of groups a) through h), a nonionic surfactant with a molecular weight of less than 6000 g/mol and having silicon-containing groups plus optionally another fluorosurfactant are preferred.

Compositions containing organopolysiloxanes as curable polymer systems are especially preferred for use here. Such compositions are known from DE 34 10 646 A1, for example. It is known that a distinction is made between organopolysiloxanes that crosslink by means of an addition reaction, organopolysiloxanes that crosslink by means of a condensation reaction and organopolysiloxanes that crosslink by means of a ring-opening metathesis reaction. All these polymer systems may be used according to the invention.

Organopolysiloxanes that crosslink by means of an addition reaction are preferred. Organopolysiloxanes that cure by means of an addition reaction are known from DE 34 10 646 A1, DE 100 17 154 A1, for example.

These compositions are usually used in the form of a multicomponent dental impression compound containing components A and B, in which a) component A contains an organopolysiloxane having at least 2 ethylenically unsaturated groups and a hydrosilylation catalyst, b) component B contains an organohydrogen polysiloxane, and c) at least one of components A and/or B contains the fluorosurfactant of groups a) through h), the silicon-containing nonionic surfactant and optionally an additional fluorosurfactant.

Organopolysiloxanes having at least 2 allyl or especially vinyl groups bound to Si atoms are usually used as the organopolysiloxane with at least 2 ethylenically unsaturated groups.

These are typically compounds of the formulas XIV or XV

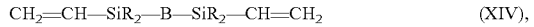

$$CH_2=CH-SiR_2-B-SiR_2-CH=CH_2 \quad (XIV),$$

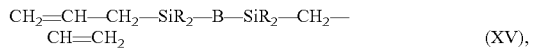

$$CH_2=CH-CH_2-SiR_2-B-SiR_2-CH_2-CH=CH_2 \quad (XV),$$

where B is a group of formula $-O-(SiR_2-O)_{m2}-$,
the individual R groups within the polymer chain denote, independently of one another, alkyl, alkenyl, alkynyl, cycloalkyl, aryl and/or aralkyl, which are optionally substituted, and m2 is an integer from 10 to 6000, preferably from 20 to 2000.

Organopolysiloxanes having at least 2 ethylenically unsaturated groups are usually used as mixtures of polymers of different chain lengths. Typical molecular weights (number average) vary in the range from 900 to 500,000, preferably from 1500 to 150,000.

Examples of alkyl groups include linear or branched alkyl groups with 1 to 6 carbon atoms such as methyl, ethyl, n-propyl, isopropyl or n-butyl.

Examples of substituted alkyl groups include linear or branched alkyl groups with 1 to 6 carbon atoms substituted with one or more halogen atoms, e.g., trifluoromethyl.

Examples of cycloalkyl groups include groups with 5 to 6 ring carbon atoms such as cyclohexyl.

Examples of aryl groups include monocyclic or bicyclic aromatic hydrocarbon groups such as phenyl or naphthyl.

Examples of substituted aryl groups include alkyl- or halogen-substituted phenyls such as tolyl, xylyl or chlorophenyl.

One example of an aralkyl group is benzyl.

Organopolysiloxanes of formulas I and/or II, in which R is methyl, are especially preferred.

The compounds generally used as crosslinking agents are used as organohydrogen polysiloxanes. These may be polyalkyl, polyaryl, polyalkylaryl, polyhaloalkyl, polyhaloaryl and polyhaloalkylaryl siloxanes which have at least 2 hydrogen atoms bound to silicon atoms in the molecule.

A typical example here would be compounds of formula $R_a H_b SiO_{(4-(a+b)/2)}$, where R has the meanings given above for the compounds of formulas XIV or XV, a is a real number, where $1<a<2$, b is a real number, where $0<b\leq 1$, with the provision that $1<a+b<2.7$ and that the compounds have at least 2Si—H bonds, preferably at least 3Si—H bonds.

Preferred examples of organohydrogen polysiloxanes include the compounds of formulas XVIa, XVIb, XVIc, XVId and XVIe

$$H-SiR_2-O-(SiR_2-O)_c-(SiHR-O)_d-SiR_2H, \quad (XVIa)$$

$$R_3Si-O-(SiR_2-O)_c-(SiHRO)_d-SiR_3, \quad (XVIb)$$

$$R_{n3}Si-(O-SiR_2-H)_{4-n3}, \quad (XVIc)$$

$$(SiO_{4/2})_q(R_2HSiO_{1/2})_p, \quad (XVId)$$

(XVIe)

where R has the meanings defined for compounds of formulas XIV or XV, and different R groups may assume different meanings within one molecule within the scope of the given definition, in particular alkyl groups, preferably methyl, $R^{35}$ to $R^{40}$, independently of one another, denote hydrogen, alkyl, cycloalkyl, aryl or aralkyl, where at least 2 of these groups denote hydrogen and of the groups $R^{35}$ and $R^{36}$ or $R^{37}$ and $R^{38}$ or $R^{39}$ and $R^{40}$ only one is hydrogen, c, d and e, independently of one another, are integers from 0 to 100, where the sum of c, d and e is 2 to 300, n3 is an integer from 0 to 3, q and p, independently of one another, are real numbers greater than 0, with the provision that the sum of q and p is 1, and n4 is an integer from 1 to 5, preferably 1 or 2.

Organohydrogen polysiloxanes having an SiH content of 0.01 to 15 mmol/g preferably 0.1 to 10 mmol/g are preferred.

Additional organohydrogen polysiloxanes preferred for use are methyl hydrogen polysiloxane.

The catalysts used for hydrosilylation are usually salts, complexes or colloidal forms of the transition metals of side group 8. Platinum, palladium or rhodium is preferably used in the form of metals or as complexes. Platinum complexes prepared from hexachloroplatinic acid or from platinum salts, for example, tris(divinyltetramethyldisiloxane)diplatinum(o) complex, platinum divinyltetramethyldisiloxane complex are especially preferred for use here.

Especially preferred compositions contain a polydialkylsiloxane with at least 2 vinyl groups and a platinum compound as the hydrosilylation catalyst in component A.

Other especially preferred compositions contain in component B the fluorosurfactant of groups a) through h) in combination with a silicon-containing nonionic surfactant and optionally in combination with another fluorosurfactant.

Other preferred compositions contain organopolysiloxanes that crosslink by means of a condensation reaction.

Organopolysiloxanes that are curable by condensation reaction are disclosed in DE 41 37 698 A1, for example.

Compositions in which component C contains a polydialkylsiloxane with at least 2 hydroxyl groups and whose component D contains a polydialkylsiloxane and/or a silane with at least 2 di- or trialkoxysilyl groups and a condensation catalyst, preferably a tin compound are preferred.

Also preferred are compositions in which component D contains the fluorosurfactant of groups a) through h) in combination with a silicon-containing nonionic surfactant and optionally in combination with another fluorosurfactant.

These are generally used in the form of a multicomponent dental impression compound which contains components C and D, in which d) component C contains an organopolysiloxane with at least 2 hydroxyl groups,
e) component D contains a silicic acid ester, polysilicic acid ester and/or an organopolysiloxane with at least 2 alkoxy groups and a condensation catalyst and
f) at least one of the components C and/or D contains the fluorosurfactant of groups a) through h), a silicon-containing nonionic surfactant and optionally another fluorosurfactant.

Usually organopolysiloxanes having at least 2 hydroxyl groups bound to Si atoms are used as the organopolysiloxane with at least 2 hydroxyl groups.

Typically these are compounds of the following formula XVII

$$HO-SiR_2-B-SiR_2-OH \quad (XVII),$$

where B has the meaning defined for the compounds of formula XIV and XV.

Organopolysiloxanes with hydroxyl end groups in which R is methyl are especially preferred.

Organopolysiloxanes with at least 2 hydroxyl groups are usually used as mixtures of polymers of different chain lengths. Typical molecular weights (number average) vary in the range of 900 to 500,000, preferably from 1500 to 150,000.

Organopolysiloxanes or organooxysilicon compounds having at least two, preferably 3 or 4 alkoxy groups bound to Si atoms are generally used as the silanes, silicic acid esters, polysilicic acid esters and/or organopolysiloxanes having at least 2 alkoxy groups.

These are typically compounds of the following formulas XVIII and/or XIX and/or XX

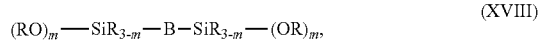
$$(RO)_m-SiR_{3-m}-B-SiR_{3-m}-(OR)_m, \quad (XVIII)$$

$$SiR_z(OR')_{4-z}, \quad (XIX)$$

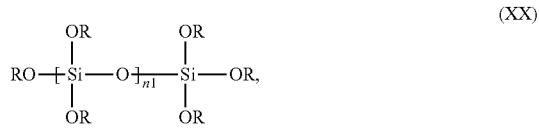
$$RO-\!\!\left[\!\!\begin{array}{c}OR\\|\\Si-O\\|\\OR\end{array}\!\!\right]_{\!\!n1}\!\!\begin{array}{c}OR\\|\\Si-OR,\\|\\OR\end{array} \quad (XX)$$

where B has the meaning defined for compounds of formulas XIV and XV, the individual R groups within the polymer chain of formula XVIII or XIX or within the compounds of formula XX, independently of one another, denote alkyl, cycloalkyl, aryl and/or aralkyl, which are optionally substituted, the individual R' groups within the compounds of formula XIX, independently of one another, have one of the meanings defined for R, preferably alkyl, z is an integer from 0 to 2,
n1 is an integer from 1 to 100, preferably 50 to 70,
and m is an integer from 1 to 3.

Examples of R groups are given in the description of the vinyl- and allyl-terminated organopolysiloxane of formulas XIV and XV.

Alkoxysilicon compounds of formula XIX, in which R and R' are methyl and z is 0, 1 or 2, are especially preferred.

Organopolysiloxanes with at least 2 alkoxy groups are usually used as mixtures of polymers of different chain length. Typical molecular weights (number average) vary in the range of 400 to 10,000, preferably 250 to 5000.

Catalysts used for the condensation reaction are usually organotin compounds, titanates, zirconates or bismuthates, for example, tetraethyl titanate, tetraisopropyl titanate, tetra-n-propyl titanate, tetra-n-butyl titanate, n-butyl polytitanate, tetra-2-ethylhexyl titanate, tetraisooctyl titanate, octylene glycol titanate, tetra-n-propyl zirconate, tetra-n-butyl zirconate, tin(II) isooctoate, dioctyltin dicarboxylate, dioctyltin dilaurate, dibutyltin dilaurate, organotin carboxylate, dibutyltin carboxylate, dibutyltin acetylacetonate, dibutyltin diacetate and bismuth(II) ethylhexanoate.

Other preferred compositions contain polyethers having alkenyl groups.

Curable systems of this type are known from DE-A-40 10 281 for example.

Compositions in which component E contains a (poly)alkylene ether with at least 2 alkylene groups and a platinum compound as the hydrosilylation catalyst are preferred.

Also preferred are compositions, in which component F contains the fluorosurfactant of groups a) through h) and optionally another fluorosurfactant and/or optionally a silicon-containing nonionic surfactant.

These are usually used in the form of a multicomponent dental impression compound, which contains components E and F, in which g) component E contains a crosslinking catalyst,
h) component F contains a crosslinkable polyether having alkenyl groups and an organohydrogen polysiloxane and/or SiH polyether, and
i) at least one of the components E and/or F contains the fluorosurfactant of groups a) through h), a silicon-containing nonionic surfactant and optionally another fluorosurfactant.

Polymers derived from (poly)alkylene glycols and terminated with ethylenically unsaturated groups, e.g., with allyl ether groups are usually used as the alkenyl group-containing polyethers.

Typically these are compounds of the following formula XXI

$$X\text{-}A\text{-}(X)_{n1} \quad (XXI),$$

where A and n1 have the meanings defined for compounds of formula XI, and X is an alkenyl group with a terminal double bond.

Examples of alkenyl groups with a terminal double bond X include —CH$_2$—CH=CH$_2$, —SiR$_2$—CH=CH$_2$, —CR$_2$—CH=CH$_2$ and —C$_6$H$_4$—CH=CH$_2$, where R denotes alkyl groups.

Polyethers of formula XXI having ethylene oxide and/or propylene oxide units, in particular those with terminal allyl groups are especially preferred.

Polyethers having alkenyl groups are generally used as mixtures of polymers of different chain lengths. Typical molecular weights (number average) vary in the range of 150 to 3,000,000, preferably from 250 to 100,000.

The organohydrogen polysiloxanes that may be used include the compounds described above in the description of the organopolysiloxanes that crosslink by means of an addition reaction.

Organohydrogen polysiloxanes having an SiH content of 0.01 to 15 mmol/g, preferably 0.1 to 10 mmol/g are also preferred for use in this crosslinkable polymer system.

Other preferred organohydrogen polysiloxanes for use here include methyl hydrogen polysiloxanes.

The SiH polyethers may be compounds of the formula XXII

Y-A-(Y)$_{n1}$ (XXII), where A and n1 have the meanings defined for compounds of formula XI and Y is a group containing a silane group.

Examples of Y groups include groups of the formula —R'—SiR$_2$H or the formula XVIf

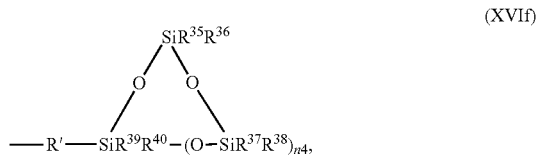

(XVIf)

where R' stands for an alkylene group, preferably with 1 to 6 carbon atoms,
R has the meanings defined for compounds of formula XIV or XV and different groups R may assume different meanings within one molecule within the scope of the given definition, in particular denoting alkyl groups, preferably methyl, and R$^{35}$ to R$^{40}$ as well as n4 have the meanings defined above for groups of formula XVIe.

In this curable system, the salts and complexes described above or colloidal forms of transition metals of side group 8 are also used as catalysts. Platinum, palladium or rhodium in the form of metals or complexes is preferred for use here.

Platinum complexes prepared from hexachloroplatinic acid or from platinum salts are especially preferred, e.g., tris(divinyltetramethyldisiloxane)diplatinum(o) complex, platinum divinyltetramethyldisiloxane complex.

Other preferred compositions contain polyethers having alkoxysilyl groups.

Curable systems of this type are disclosed in PCT/EP2005/001470 and EP-A-1 226 808, for example.

Compositions containing a polyalkylene ether with at least 2 alkoxysilyl groups and a tin compound and/or organic acids and/or bases and/or the salts thereof as the condensation catalyst are preferred.

Curable systems of this type are preferably used in the form of a multicomponent dental impression compound containing components G and H, in which j) component G contains a crosslinkable polyether having alkoxysilyl groups,
k) component H contains water,
l) at least one of the components G and/or H contains a catalyst as well as the fluorosurfactant of groups a) through h), a nonionic surfactant containing silicon and optionally another fluorosurfactant.

Polymers derived from polyalkylene glycols and terminated with alkoxysilane groups, optionally via a bridge group, are generally considered for use as the polyethers having alkoxysilyl groups.

These are typically compounds of formula XXIII

(RO)$_{3-n5}$R$_{n5}$Si—BG2-A-(BG2-SiR$_{n5}$(OR)$_{3-n5}$)$_{n1}$ (XXIII), where A and n1 have the meanings defined for compounds of formula XI,
BG2 stands for a covalent bond or a bridge group not including —O—,
n5 stands for an integer from 0 to 2,
R has the meanings defined for compounds of formulas XIV or XV, and different groups R, Br and different indices n5 within one molecule may assume different meanings within the scope of the given definitions, R denotes in particular alkyl groups, preferably methyl, and BG2 is in particular a covalent bond or a bridge group —O—CO—NH—R'—, where R' is attached to the silicon atom and denotes an alkyl group, preferably methyl, ethyl or propyl.

Polyethers having alkoxysilyl groups may also be used as mixtures of polymers of different chain lengths. Typical molecular weights (number average) vary in the range of 150 to 3,000,000, preferably from 250 to 100,000 and especially preferably 250 to 50,000.

In this curable system, the organotin compounds described above, such as dibutyltin dilaurate, may be used as the catalysts. However, organic acids such as toluenesulfonic acid or organic bases such as amines, guanidines, DBU or DGN or salts of these acids or bases may also be used.

Other preferred compositions contain polyethers having aziridino groups.

Curable systems of this type are known from U.S. Pat. No. 4,353,242 for example.

Preferred compositions contain crosslinkable polyethers having groups derived from an ethylenically unsaturated carboxylic acid or alkenyl radials as crosslinkable groups or have groups crosslinkable by means of a ring-opening metathesis reaction as well as having at least one fluorosurfactant of groups a) through h) as defined above, optionally in combination with another fluorosurfactant and/or optionally in combination with a nonionic surfactant having silicon.

Especially preferred compositions of this type contain crosslinkable polyethers having alkoxysilyl groups or aziridino groups as crosslinkable groups.

With these compositions, polyethers containing polyols and/or alkenyl groups and/or alkynyl groups and/or hydroxyl- and/or alkoxy-terminated polyethers are preferably also used as additional components.

However, mixtures of silicon-containing nonionic surfactants and fluorosurfactants of groups a) through h), optionally in combination with the above-mentioned additional polyol and/or polyether components, are preferably used in these compositions.

Curable systems of this type are generally used in the form of a multicomponent dental impression compound that contains components I and J, in which m) component I contains a crosslinkable polyether having aziridino groups or alkoxysilyl groups or a polyether having groups crosslinkable by means of a ring-opening metathesis reaction, n) component J contains a catalyst, and
o) at least one of components I and/or J contains a fluorosurfactant of groups a) through h), a silicon-containing nonionic surfactant and optionally another fluorosurfactant.

Polymers derived from polyalkylene glycols and terminated with alkoxysilyl groups or with aziridino groups via a bridge group are usually used as the polyethers that contain aziridino groups or alkoxysilyl groups.

These are typically compounds of the following formula XXVIII $$\text{(XXVIII)}$$

where A and n1 have the meanings defined for formula XI, R has the meanings defined for compounds of formulas XIV or XV, and different groups R within a molecule may assume different meanings within the scope of the given definition, and R denotes in particular alkyl groups, preferably methyl.

Polyethers having aziridino groups are generally used as mixtures of polymers of different chain lengths. Typical molecular weights (number average) vary in the range of 150 to 3,000,000, preferably 250 to 100,000 and especially preferably 250 to 50,000.

Sulfonium salts may be used as the catalysts in this curable system.

Other preferred compositions contain polyethers having ester groups of an ethylenically unsaturated carboxylic acid.

Curable systems of this type are described in EP 0 170 219 A2, for example.

Preferred compositions contain a crosslinkable (poly)alkylene ether having groups derived from acrylic acid and/or methacrylic acid, a heat- or radiation-activatable initiator and a nonionic surfactant containing the fluorosurfactant of groups a) through h) and optionally another fluorosurfactant and/or optionally a silicon.

These compositions may be used as single-component formulations or as two-component formulations.

Single-component dental impression compounds, which are cured by UV radiation and/or heat, are preferred for use here. In addition to the curable polymer system as well as the surfactant used according to the invention, these generally contain photoinitiators.

Polymers derived from polyalkylene glycols and terminated with ethylenically unsaturated carboxylic acids are generally used as the crosslinkable polyethers.

These are typically compounds of formulas XXIV and/or XXVIII $$R^{50}\text{-A-(CO—}R^{50})_{n1} \quad \text{(XXIV)},$$

$$R^{50}\text{—CO-A-(CO—}R^{50})_{n1} \quad \text{(XXVIII)}$$

where A and n1 have the meanings defined for the compounds of formula XI, $R^{50}$ is an ethylenically unsaturated group, preferably an alkylene group, and the $R^{50}$ groups within a molecule may be different within the scope of the meanings given.

$R^{50}$ is most especially preferably $CH_2$=CH— or $CH_2$=C($CH_3$)—, i.e., a group derived from acrylic acid or methacrylic acid.

Polyethers having ethylenically unsaturated carboxylic acid ester groups are generally used as mixtures of polymers of different chain lengths. Typical molecular weights (number average) vary in the range of 150 to 3,000,000, preferably 250 to 100,000 and especially preferably 250 to 50,000.

These polyethers are usually cured by electromagnetic radiation, preferably UV radiation or visible light. In this curable system, e.g., camphor quinine and/or amines may be used as photoinitiators.

Preferably peroxide curing agents, optionally in combination with amines, are used in heat-curing systems.

Other preferred compositions contain polyethers, polysiloxanes and/or synthetic rubbers containing groups that can be crosslinked by means of a ring-opening metathesis polymerization (ROMP). Curable systems of this type are known from EP 1 317 917 A1, U.S. Pat. No. 6,649,146 B2, WO 02/32338 A2 and U.S. Pat. No. 6,455,029, for example.

These are generally used in the form of a multicomponent dental impression compound containing components K and L, in which
p) component K contains polyethers, polysiloxanes and/or synthetic rubbers having groups crosslinkable via ROMP,
q) component L contains a ROMP-crosslinking catalyst, and
r) at least one of the components K and/or L contains the fluorosurfactant of groups a) through h) and optionally another fluorosurfactant and/or optionally a silicon-containing nonionic surfactant.

Examples of polyethers, polysiloxanes and/or synthetic rubbers having groups crosslinkable via ROMP usually include polymers derived from (poly)alkylene glycol, polydialkyl or arylsiloxanes and/or polyalkenes or polyalkanedienes, and provided with unsaturated terminal and/or side chain groups MT bound via a spacer B.

These polysiloxanes are typically compounds of the following formula XXV $$\text{MT-BG-}(SiR_2O)_{m5}\text{—}(SiR(MT)O)_{n6}\text{-BG-MT} \quad \text{(XXV)},$$

where R independently of one another denote alkyl, cycloalkyl, aryl and/or aralkyl, optionally substituted,
m5 is an integer from 10 to 60,000, preferably from 20 to 2000,
m6 is an integer from 0 to 100, preferably from 0 to 10,
BG is a bridge group,
MT is a group crosslinkable via ROMP and
the groups MT, B2 and R as well as the indices m5 and/or n6 may assume different meanings within a molecule within the scope of the given meanings.

Typical molecular weights (number average) of compounds of formula XXV vary in the range of 900 to 500,000, preferably 1500 to 150,000.

Organopolysiloxanes with at least 2 ethylenically unsaturated groups usually occurs mixtures of polymers of different chain lengths. Typical molecular weights (number average) vary in the range of 900 to 500,000, preferably 1500 to 150,000.

Organopolysiloxanes of formulas XXV in which R is methyl are especially preferred.

The (poly)alkylene glycols are typically compounds of the following formulas XXVI and/or XXIX $$\text{MT-BG3-}(C_{n6}H_{2n6}O)_{m6}\text{—}(C_{n6}H_{2n6-1}(BG3\text{-MT})O)_{m7}\text{—BG3-MT} \quad \text{(XXVI)},$$

$$\text{MT-BG3-A-(BG3-MT))}_{n1} \quad \text{(XXIX)},$$

where A and n1 have the meanings defined for compounds of formula XI,
n6 is an integer from 4 to 8, preferably 2 to 4,
m6 is an integer from 2 to 70,000, preferably 10 to 2500,
m7 is an integer from 0 to 70,000, preferably 10 to 2500, the sum of m6 and m7 is from 3 to 70,000, preferably 10 to 2500,
BG3 is a bridge group,
MT is a group crosslinkable via ROMP and
the groups MT and BG3 as well as the indices n6, m6 and/or m7 may be different within one molecule within the scope of the given meanings.

The synthetic rubbers are typically compounds of the following formula XXVII

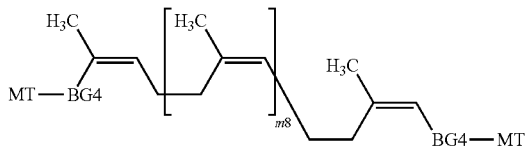

(XXVII)

where BG4 denotes a bridge group,
MT is a group crosslinkable via ROMP, and
m8 is an integer from 1500 to 30,000, preferably 20 to 500.

In addition to 1,4-cis and 1,4-trans and their mixed forms, polymers of 1,3-dienes, for example, 2,3-dimethyl-1,3-butadiene, polybutadiene and poly-(2-chloro-1,3-butadiene) as well as synthetic rubbers obtained by copolymerization of 2 or 3 different monomers are formed. The most important synthetic rubbers include styrene-butadiene rubber, acrylonitrile-butadiene rubber and isobutene-isoprene rubber, ethylene-propylene copolymers (EPM), ethylene-propylene-diene terpolymers (EPDM) as well as elastomers based on polyurethane, polysulfides and chlorosulfonylpolyethylene, and the synthetic rubber may also be crosslinked by vulcanization.

The unsaturated ROMP-crosslinkable groups MT are, for example, cycloalkenyl groups, e.g., cyclobutenyl, cyclopentenyl or groups of the general formula

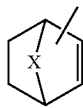

where X=O, S, NH or a saturated or unsaturated $C_1$-$C_{30}$ hydrocarbon group.

The bridge group BG4 in the formulas listed above is preferably —O— or alkylene, in particular —$CH_2$—, —$CH_2CH_2$—, —$CH_2CH_2CH_2$— or —$CH(CH_3)$—$CH_2$—.

In this curable system, the catalysts used are salts, complexes or colloidal forms of the transition metals of side group 8. Ruthenium, osmium, tungsten or molybdenum is preferably used in the complexes. Especially preferred are ruthenium carbene complexes, e.g., the Grubbs catalyst.

The inventive compositions containing curable polymers selected from the group of organopolysiloxanes that crosslink by means of an addition reaction, organopolysiloxanes that crosslink by means of a condensation reaction, polyethers that crosslink by means of a condensation reaction and contain alkoxysilyl groups, polyethers that crosslink by means of an addition reaction and contain aziridino groups, polyethers that crosslink by means of an addition reaction and contain alkenyl groups, polyethers that crosslink by means of a radical polymerization reaction and contain ester groups of an ethylenically unsaturated carboxylic acid or polyethers, silicones or rubbers that crosslink by means of a ring-opening metathesis reaction, preferably contain as an additional component a polyether having an alkenyl group and/or a hydroxyl-terminated or alkoxy-terminated polyether. This additional component causes a further improvement in the contact angle properties of the uncured plastic material and thus yields a further improvement in the precision of detail of the resulting impression.

Examples of preferred additives of this type include the compounds of formulas XI, XII and XIII described above.

The inventive compositions may also contain, in addition to the crosslinkable polymers and the fluorosurfactant of groups a) through h) or the surfactant mixture, additional components which are usually used in such compositions.

Examples of such additional components include fillers. These may be reinforcing fillers or nonreinforcing fillers or mixtures thereof.

Suitable reinforcing fillers include in particular highly disperse active fillers having a BET surface area of at least 50 $m^2$/g. Especially suitable are those having an individual particle size in the nanometer range, which may be present as aggregates and/or agglomerates. Preferred reinforcing fillers are substances selected from the group consisting of aluminum hydroxide, zinc oxide, titanium dioxide, zirconium oxide, silicon dioxide and precipitated and/or pyrogenic silica. The aforementioned compounds may of course be used individually or in any combination with one another, namely in both hydrophilic and hydrophobic forms.

The at least one reinforcing filler is preferably also present in the form of nanoparticles, in fibrous or flakey form, e.g., as a mineral, fibrous filler or as a synthetic fibrous filler.

The amount of reinforcing filler in the inventive composition is usually 0 to 80 wt %, preferably 0.1 to 50 wt % and especially preferably 0.1 to 40 wt %, based on the total composition.

In principle, the same substances as those used for the reinforcing fillers are suitable for use as the nonreinforcing fillers, but the nonreinforcing fillers necessarily have a BET surface area of less than 50 $m^2$/g (Degussa Pigment Monograph Silicic Acids, No. 12, page 5 and No. 13, page 3). Preferred nonreinforcing fillers are substances selected from the group consisting of alkaline earth metal oxides, alkaline earth metal hydroxides, alkaline earth metal fluorides, alkaline earth metal carbonates, calcium apatite ($Ca_5[(F, Cl, OH, \frac{1}{2}CO_3)/(PO_4)_3]$ in particular calcium hydroxyapatite ($Ca_5[(OH)/(PO_4)_3]$, titanium dioxide, zirconium oxide, aluminum hydroxide, silicon dioxide, precipitated silica and calcium carbonate. The aforementioned compounds may of course be used either individually or in any combination with one another, namely in both hydrophilic and hydrophobic forms.

The nonreinforcing fillers that are used preferably have an average grain size of greater than 0.1 µm (*Ullmann's Enzyclopädie der Technischen Chemie* [Encyclopedia of Industrial Chemistry], vol. 21 page 523).

The amount of nonreinforcing filler in the inventive composition is usually 0 to 80 wt %, preferably 0.1 to 50 wt % and especially preferably 0.1 to 40 wt %, based on the total composition.

The total amount of reinforcing and nonreinforcing filler in the inventive composition is usually 0 to 80 wt %, preferably 0.01 to 80 wt %, especially preferably 0.05 to 75 wt % and most especially preferably 0.1 to 70 wt %, based on the total composition.

The inventive compositions may also contain one or more of the following additives: buffer salts, water scavengers, paste forming agents, additional surfactants, active ingredients, plasticizers, optical scan-enabling substances, taste and/or odor substances, diagnostics-enabling substances, fluoridation agents, bleach substances, desensitizing agents, adhesion promoting agents, dyes, indicators, stabilizers (antioxidants) and antibacterial substances.

If the inventive composition is in the form of a multicomponent system, then it is preferably apportioned in tailored amounts for subsequent use and especially preferably stored in cartridges and tube bags as described in EP-A-0 723 807, EP-A-0 541 972, WO 98/44860 A1, EP-A-0 492 412, EP-A-0 492 413 and EP-A-0 956 908, for example.

Most especially preferred are compositions containing
a) 25 to 85 wt % organopolydialkylsiloxane with at least 2 alkenyl groups,
b) 1 to 70 wt % organohydrogen polysiloxane with an SiH content of 0.1 to 15.0 mmol/g,
c) 0.0001 to 2 wt % hydrosilylation catalyst, especially salts, complexes and colloidal forms of the transition metals of side group 8,
d) 0 to 90 wt % nonreinforcing fillers with a BET surface area of less than 50 $m^2/g$,
e) 0.1 to 50 wt % reinforcing fillers with a BET surface area equal to or greater than 50 $m^2/g$,
f) 0 to 20 wt % additives and auxiliaries, such as plasticizers, dyes, stabilizers, inhibitors, alkyl-capped fatty alcohol ethoxylates, etc.
g) 0.01 to 5.0 wt % nonionic polyether siloxane surfactant with 3 to 7 silicon atoms in the siloxane substructure and/or nonionic polyether carbosilane surfactant with 1 to 7 silicon atoms in the carbosilane substructure and an alkylene oxide content of 1 to 20 units, and
h) 0.001 to 5.0 wt % of the fluorosurfactant described above, selected from the groups a) through h) where the ratio of the surfactants g) and h) is preferably 100:1 to 1:100, especially 50:1 to 1:50, most especially preferably 10:1 to 1:10 and especially preferably 5:1 to 1:5.

Two-component compositions containing components a) through h) as defined above in the quantities indicated plus i) 0.1 to 25 wt %, preferably 0.1 to 10.0 wt %, especially preferably 0.5 to 5.0 wt % and most especially preferably 0.5 to 2.5 wt % branched or linear alkyl-, hydroxy-, alkynyl- and/or alkenyl-terminated (poly)alkylene ethers and/or mixtures thereof are especially preferred, where the weight ratio of organopolysiloxanes a) to polyether i) is preferably 1:1 to 80:1, especially preferably 1:1 to 60:1, most especially preferably 1:1 to 40:1 and in particular preferably 1:1 to 30:1.

Two-component compositions containing components a) through h) as defined above in the stated quantities plus k) 0.1 to 25 wt % preferably 0.1 to 10.0 wt %, especially preferably 0.5 to 5.0 wt % and most especially preferably 0.5 to 2.5 wt % of a polyol or a mixture of polyols are especially preferred.

Two-component compositions containing the components a) through h) as defined above in the stated quantities plus the components i) and k) as defined above in the stated quantities are most especially preferred.

Two-component compositions consisting of components A and B are most especially preferred, wherein component A contains
a) 10 to 80 wt % organopolydialkylsiloxane with at least 2 alkenyl groups,
c) 0.0001 to 2 wt % hydrosilylation catalyst, in particular salts, complexes and colloidal forms of the transition metals of side group 8,
d) 0 to 90 wt % nonreinforcing fillers with a BET surface area of less than 50 $m^2/g$,
e) 0.1 to 50 wt % reinforcing fillers with a BET surface area of greater than or equal to 50 $m^2/g$,
f) 0 to 20 wt % auxiliaries and additives, such as plasticizers, dyes, stabilizers and/or inhibitors, and
j) 0.001 to 5.0 wt % alkyl-, aryl-, aralkyl-capped nonionic surfactants, preferably alkyl-capped fatty alcohol ethoxylates, silicone surfactants, polyether carbosilanes, carbosilane surfactants and fluorosurfactants, which are alkyl-capped, and especially alkyl-capped fatty alcohol ethoxylates,
and component B contains
a) 0.1 to 70 wt % organopolydialkylsiloxane with at least 2 alkenyl groups,
b) 1.2 to 80 wt % organohydrogen polysiloxane with an SiH content of 0.1 to 15.0 mmol/g,
d) 0 to 90 wt % nonreinforcing fillers with a BET surface area of less than 50 $m^2/g$,
e) 0.1 to 50 wt % reinforcing fillers with a BET surface area greater than or equal to 50 $m^2/kg$,
f) 0 to 20 wt % auxiliaries and additives, such as plasticizers, dyes, stabilizers and/or inhibitors,
g) 0.01 to 10.0 wt % nonionic polyether siloxane surfactant with 3 to 7 silicon atoms in the siloxane substructure and/or nonionic polyether carbosilane surfactant with 1 to 7 silicon atoms in the carbosilanes substructure and an alkylene oxide content of 1 to 20 units,
h) 0.001 to 10.0 wt % of the fluorosurfactant described above, selected from groups a) through h), where the ratio of the surfactants g) and h) is preferably 25:1 to 1:25, especially preferably 20:1 to 1:5, most especially preferably 10:1 to 1:5 and in particular preferably 5:1 to 1:3 and
i) 0.5 to 50 wt % branched or linear alkyl or alkynyl and/or alkenyl and/or hydroxy-terminated (poly)alkylene ethers and/or mixtures thereof, where the weight ratio of organopolysiloxane a) to polyether i) is 1:50 to 50:1, preferably 10:1 to 1:10 and in particular preferably 4:1 to 1:5.

Also especially preferred are two-component compositions consisting of components A and B in which component A contains
a) 10 to 80 wt % organopolydialkylsiloxane with at least 2 alkenyl groups,
c) 0.0001 to 2 wt % hydrosilylation catalyst, in particular salts, complexes and colloidal forms of the transition metals of side group 8,
d) 0 to 90 wt % nonreinforcing fillers with a BET surface area of less than 50 $m^2/g$,
e) 0.1 to 50 wt % reinforcing fillers with a BET surface area greater than or equal to 50 $m^2/kg$,
f) 0 to 20 wt % auxiliaries and additives, such as plasticizers, dyes, stabilizers and/or inhibitors and
j) 0.001 to 5.0 wt % alkyl-, aryl-, aralkyl-capped nonionic surfactants, preferably alkyl-capped fatty alcohol ethoxylates, silicone surfactants, polyether carbosilanes, carbosilane surfactants and fluorosurfactants which are alkyl capped and in particular alkyl-capped fatty alcohol ethoxylates
and component B contains
a) 0.1 to 70 wt % organopolydialkylsiloxane with at least 2 alkenyl groups,
b) 1.2 to 80 wt % organohydrogen polysiloxane with an SiH content of 0.1 to 15.0 mmol/g,
d) 0 to 90 wt % nonreinforcing fillers with a BET surface area of less than 50 $m^2/g$,
e) 0.1 to 50 wt % reinforcing fillers with a BET surface area greater than or equal to 50 $m^2/kg$,
f) 0 to 20 wt % auxiliaries and additives, such as plasticizers, dyes, stabilizers and/or inhibitors,
g) 0.01 to 10.0 wt % nonionic polyether siloxane surfactant with 3 to 7 silicon atoms in the siloxane substructure and/or nonionic polyether carbosilane surfactant with 1 to 7 silicon atoms in the carbosilane substructure and an alkylene oxide content of 1 to 20 units, h) 0.001 to 10.0 wt % of the fluorosurfactant described above, selected from groups a) through h), where the ratio of the surfactants g) and h) is preferably 25:1 to 1:25, especially preferably 20:1 to 1:5, most especially preferably 10:1 to 1:5 and in particular preferably 5:1 to 1:3 and k) 0.5 to 50 wt % polyol or mixtures of polyols.

Other especially preferred two-component compositions contain components a) through h) as defined above in the stated quantities and also components i) and k) as defined above in the stated amounts.

The quantity amounts in the above embodiment are each based on the total weight of component A or component B.

Another subject of the present invention relates to mixtures obtainable by mixing individual components of multicomponent compounds of the curable composition described above. A basic component is preferably mixed with a catalyst component in a ratio of 1:2 to 20:1, especially preferably from 1:1 to 10:1 and most especially preferably 10:1, 5:1, 4:1, 2:1 and 1:1. These mixtures are characterized by excellent wettability and excellent flow behavior on moist dental and tissue substance. Despite these good hydrophilic properties, the material does not swell up on coming in contact with aqueous media such as water, saliva, blood, disinfectant bath or aqueous gypsum paste. Good initial wettability of the mixtures is important for detailed molding of the impression material in the patient's mouth during processing and the initial contact with the moist oral/dental substance and is expressed by an extremely low contact angle which develops rapidly after mixing of the components and/or after the start of curing. The inventive compositions are characterized in that contact angles of ≤10° are achieved between 30 seconds after the start of mixing of the components of the curable polymer system, e.g., the catalyst component and the basic component, or the triggering of curing by irradiation until the curable polymer system sets up at a water droplet age within the first 10 seconds, preferably within the first 5 seconds after placing the water droplet on the surface of the dental impression material. The contact angles are measured with a G40/G23M contact angle measuring device from the company Krüss at 23° C.±1° C. with a "sessile droplet" measurement method. The measurement was performed at 50% relative atmospheric humidity.

To do so, dynamic contact angle determinations were performed at room temperature 23° C.±1° C. on the sessile droplet using the DSA100 droplet contour analysis system (Krüss, D-Hamburg) contact angle measuring device, which was combined with a fully automatic droplet dosing system. The measurement was also performed at 50% relative atmospheric humidity.

Wetting was initiated 40 seconds, 60 seconds, 90 seconds and 120 seconds after the start of mixing of the respective two-component dental impression material, i.e., during its processing time, by placing a water droplet having a volume of 2 μL on the polymerizing surface. The dynamic change in the droplet geometry was determined with a resolution of 10 images per second for the duration of a single measurement of 180 seconds and was evaluated using the manufacturer's software. The contact angles of the individual images were determined by the "circle fit" method as the average contact angle from the right and left contact angle of the individual droplet contours.

Furthermore, the cured impression material at the time of casting with plaster (immediately or 2 hours after curing) is characterized by a contact angle of less than 10° with a water droplet age within the first 10 seconds, preferably 5 seconds after placing the water droplet on the surface of the dental impression material.

The invention also relates to the cured impression material which is obtained by curing the compositions described above. The cured impression material is characterized by excellent mechanical properties and fulfills all the requirements according to ISO 4823 on an elastomeric dental impression material.

The invention also relates to the use of the fluorosurfactants described above selected from groups a) through h), optionally in combination with additional fluorosurfactant and in combination with silicon-containing nonionic surfactant having at least one (poly)alkylene oxide group and a molecular weight of less than 6000 g/mol for producing dental compounds, in particular dental impression compounds.

The invention also relates to the use of the curable compositions described above for production of dental compounds, in particular dental impression compounds.

The following examples illustrate the invention without restricting it.

A) Silicones that Crosslink by Means of an Addition Reaction

Synthesis Example A1

Catalyst Compound of a Two-Component Silicone Dental Impression Material that Crosslinks by Means of an Addition Reaction In a vacuum mixer, 50.00 parts of an α,ω-divinylpolydimethylsiloxane having a viscosity of 1000 mPas at 20° C., 6.00 parts of a pyrogenically prepared highly disperse hydrophobized silicic acid having a BET surface area of 170 m$^2$/g, 43.00 parts quartz meal having an average grain size of 10 μm and 1.00 parts of a platinum catalyst of the Karstedt type having a pure platinum content of 1.0% were mixed homogenously for 1.5 hours and then the mixture was degassed for 15 minutes. A thin fluid paste (ISO 4823) was obtained. The paste represents a possible catalyst component of the inventive two-component dental impression compound.

Synthesis Example A2

Basic Recipe of a Basic Compound of Two-Component Silicone Dental Impression Material that Crosslinks by Means of an Addition Reaction In a vacuum mixer, 20.00 parts of an α,ω-divinylpolydimethylsiloxane with a viscosity of 1000 mPas at 20° C., 19.00 parts of a polymethyl hydrogen siloxane with a viscosity of 200 mPas at 20° C. and an SiH content of 1.8 mmol/g were mixed homogeneously for 1.5 hours with 5.00 parts of a pyrogenically prepared highly disperse hydrophobized silicic acid with a BET surface area of 170 m$^2$/g and with 46.00 parts powdered quartz with an average grain size of 10 μm and then the mixture was degassed for 15 minutes. The resulting paste is a basic recipe of a basic component of the inventive two-component dental impression compound to which reference is made in the following examples for addition of the inventive fluorosurfactants.

Synthesis Example A3

Basic Compound of Two-Component Silicone Dental Impression Material that Crosslinks by Means of an Addition Reaction with an Inventive Fluorosurfactant In a vacuum mixer, 94.90 parts of the basic recipe from synthesis example A2 were mixed homogeneously for 15 minutes with 0.75 parts of a perfluoropolyether surfactant (Fluorolink E10 H from Solvay Solexis) with a surface tension of 23 dyn/cm at 20° C. and a molecular weight of approximately 1500 g/mol, 2.25 parts of a polyethylene oxide-modified polydimethylsiloxane (PEG-8 methicone) with a surface tension of 20.7 dyn/cm (in deionized water at 25° C. in a concentration of 1%) and a molecular weight of approximately 620 g/mol and 1.00 parts of an $\alpha,\omega$-diallylpolyethylene glycol with an average molecular weight of 2000 g/mol and 1.10 parts glycerol and then degassed for 15 minutes. A thin fluid paste (ISO 4823) was obtained. The paste is a possible basic component of the inventive two-component dental impression compound.

Example A1

Two-Component Silicone Dental Impression Compound that Crosslinks by Means of an Addition Reaction and Contains an Inventive Fluorosurfactant 50 parts of the catalyst component described in synthesis example A1 and 50 parts of the basic component described in synthesis example A3 were expressed from a cartridge (Mixpac) and mixed homogeneously in a static mixer (Mixpac).
Result:

A thin fluid dental impression compound (ISO 4823) was obtained and its contact angle was tested at various points in time within the processing period (see Tables 1A and 1B). It was found that in each phase during the processing time of the impression compound, an applied water droplet would spread completely on the surface of the impression compound within 1 to 10 seconds and wet it. Such a material is excellently suited for flowing in the patient's mouth despite the action of moist dental substance and saliva on the areas to be molded and imaging them accurately in the impression. In comparison with conventional silicone dental impression material that crosslinks by means of an addition reaction (comparative example AV1) and is not provided with the inventive fluorosurfactant, there is a definite difference in behavior of an applied water droplet on the surface of the impression material. When the inventive fluorosurfactant is added to the impression compound in any phase during the processing time of the impression compound, an applied water droplet will spread completely on the surface of the impression compound within 1 to 10 seconds and wet it, but with the unmodified commercial product, the applied water droplet will not spread on the surface of the impression compound and wet it sufficiently. The inventive material is excellently suited, in contrast with the conventional dental impression materials available on the market, for flowing onto the areas to be molded in the patient's mouth despite the action of moist dental substance, saliva and blood and then imaging these details accurately in the impression.

Comparative Example AV1

Two-Component Silicone Dental Impression Compound that Crosslinks by Means of an Addition Reaction and Contains 1.0% Fluorosurfactant According to U.S. Pat. No. 4,657,959 Table IV, Run 11

A silicone dental impression material that crosslinks by means of an addition reaction according to the example in Table IV run 11 of U.S. Pat. No. 4,657,959 was expressed from a cartridge (Mixpac) and mixed homogeneously in a static mixer (Mixpac).
Result:

A thin fluid dental impression compound (ISO 4823) whose contact angle was tested at various points in time within the processing time was obtained (see Tables 1 and 2). It was found that in no phase during the processing time of the impression compound within the measurement time of 30 seconds after applying the water droplet was a contact angle of <10° reached. The applied water droplets do not spread on the surface of the impression compound and do not wet it adequately. The equilibrium contact angle between 40 seconds and 120 seconds of age of the material (after the onset of mixing of the catalyst component and the basic component) occurred 10 seconds after applying the water droplet and was between 38° and 44°. This comparative example shows that not all combinations of surfactants lead to a synergistic effect. The equilibrium contact angles at a material age between 40 seconds and 120 seconds (after the start of mixing of the catalyst component and the basic component) occurred 10 seconds after applying the water droplet and were between 79° and 63°. This comparative example shows that when using the measurement method according to the present invention, the dental impression materials according to U.S. Pat. No. 4,657,959 a contact angle of <10° is not achieved and no spreading of water on the surface is achieved.

Comparative Example AV2

Silicone Dental Impression Material that Crosslinks by Means of an Addition Reaction with a Nonsynergistic Surfactant Mixture from the Best Silicone Surfactant (Run 2) and Fluorosurfactant (Run 11) from Example 1 of U.S. Pat. No. 4,657,959

50 parts of the catalyst component described in U.S. Pat. No. 4,657,959 and 50 parts of the basic component described in synthesis comparative example A9 were expressed from a cartridge (Mixpac) and mixed homogeneously in a static mixer (Mixpac).
Result:

A thin fluid dental impression compound (ISO 4823) was obtained, and its contact angles were tested at various points in time (see Tables 1 and 2). It was found that in no phase during the processing time of the impression compound within the measurement time of 30 seconds after applying the water droplet was a contact angle of <10° reached. The applied water droplets do not spread on the surface of the impression compound and do not wet it adequately. The equilibrium contact angle between 40 seconds and 120 seconds of age of the material (after the onset of mixing of the catalyst component and the basic component) was between 38° and 44° measured 10 seconds after applying the water droplet. This comparative example shows that not all combinations of surfactants lead to a synergistic effect.

The equilibrium contact angles at a material age between 40 seconds and 120 seconds (after the start of mixing of the catalyst component and the basic component) occurred 10 seconds after applying the water droplet and were between 39° and 50°. This comparative example shows that not all combinations of fluorosurfactants and silicone surfactants lead to a synergistic effect. Surprisingly a synergistic effect was achieved only in surfactant mixtures with certain fluorosurfactants and silicone surfactants. U.S. Pat. No. 4,657,959 does not describe any mixtures of different surfactants. If as in this comparative example, the best surfactants from the experimental series of silicone surfactants and the best from the fluorosurfactants of U.S. Pat. No. 4,657,959 are combined, no spreading of water droplets on the surface of the silicone impression material can be achieved.

B) Silicones that Crosslink by Means of a Condensation Reaction

Synthesis Example B1

Basic Compound of a Silicone Dental Impression Material that Crosslinks by Means of a Condensation Reaction and Contains an Inventive Synergistic Surfactant Mixture 97 parts of the basic compound of the commercial product Lastic 90 fine, Kettenbach GmbH+Co. KG, lot 91631 were mixed homogeneously for 15 minutes and degassed in a vacuum mixer with 1.5 parts of a perfluoropolyether surfactant (Fluorolink E10 H from Solvay Solexis) with a surface tension of 23 dyn/cm at 20° C. and a molecular weight of approximately 1500 g/mol, 1.50 parts of a polyethylene oxide-modified polydimethylsiloxane (PEG-8 methicone) with a surface tension of 20.7 dyn/cm (in deionized water, at 25° C., at a concentration of 1%) and a molecular weight of approximately 620 g/mol. A thin fluid paste (ISO 4823) was obtained. The paste is a possible basic component of the inventive two-component dental impression compound.

TABLE 1

Time-dependent contact angle measurements on silicones that crosslink by means of an addition reaction and contain inventive fluorosurfactants in comparison with the prior art

| Examples/ Comparative examples | Age of material after start of mixing 40 s[1] Period of time until reaching a contact angle of 10°[2] (s) | Age of material after start of mixing 60 s[1] Period of time until reaching a contact angle of 10°[2] (s) | Age of material after start of mixing 90 s[1] Period of time until reaching a contact angle of 10°[2] (s) | Age of material after start of mixing 120 s[1] Period of time until reaching a contact angle of 10°[2] (s) |
|---|---|---|---|---|
| Example A1 | 3 | 3 | 3 | 3 |
| Comparative example AV1 | —[3] | —[3] | —[3] | —[3] |
| Comparative example AV2 | —[3] | —[3] | —[3] | —[3] |

[1] Time of placement of the water droplet after the start of mixing of the impression material
[2] Droplet size approximately 2 μL, measurement time of droplet max. 30 s
[3] No contact angle <10° is achieved within the measurement time of 30 s after applying the droplet of water

TABLE 2

Time-dependent contact angle measurements on silicones that crosslink by means of an addition reaction and contain inventive fluorosurfactants in comparison with the prior art

| Examples/ Comparative examples | Age of material after start of mixing 40 s[1] Age of droplet 10 s[2] Contact angle (°) | Age of material after start of mixing 60 s[1] Age of droplet 10 s[2] Contact angle (°) | Age of material after start of mixing 90 s[1] Age of droplet 10 s[2] Contact angle (°) | Age of material after start of mixing 120 s[1] Age of droplet 10 s[2] Contact angle (°) |
|---|---|---|---|---|
| Example A1 | <10 | <10 | <10 | <10 |
| Comparative example AV1 | 79 | 77 | 75 | 63 |
| Comparative example AV2 | 39 | 42 | 45 | 50 |

[1] Time of placement of the droplet of water after the start of mixing of the impression material
[2] Droplet size approximately 2 μL, measurement time of droplet max. 30 s

Example B1

Silicone Dental Impression Compound that Crosslinks by Means of a Condensation Reaction and Contains an Inventive Synergistic Surfactant Mixture 7.1 parts of a catalyst paste of a silicone dental impression material (commercial product Lastic Xtra paste curing agent, Kettenbach GmbH+Co. KG, lot number 91841) that crosslinks by means of a condensation reaction and 92.9 parts of the basic component described in synthesis example B1 were mixed homogeneously for 30 seconds using a mixing spatula on a mixing block.

Result, Example B1:

A thin fluid dental impression compound (ISO 4823) was obtained, and its contact angle was determined at various points in time within the processing time (see Tables 3 and 4). It was found that in each phase during the processing time of the impression compound, a droplet of water applied would spread completely on the surface of the impression compound and wet it within ≤10 seconds. Such a material is excellently suited for flowing on the areas to be molded in the patient's mouth, despite the influence of moist dental substance and saliva, and is capable of imaging it accurately in the impression. In contrast with commercial silicone dental impression materials that crosslink by means of a condensation reaction (comparative example BV1) and have not been provided with the inventive synergistic surfactant mixture, there is a significant difference in the behavior of an applied water droplet on the surface of the impression material. Whereas with the addition of the synergistic surfactant mixture an applied water droplet will spread completely on the surface of the impression compound within ≤10 seconds and wet it in each phase during the processing time of the impression compound, but with the unmodified commercial product, the applied water droplets do not spread on the surface of the impression compound and do not adequately wet it. The inventive material is excellently suited, in contrast with the conventional dental impression materials available on the market, for flowing on the areas to be molded in the patient's mouth despite the influence of moist dental substance, saliva and blood, and imaging these areas accurately in the impression.

Comparative Example BV1

Silicone Dental Impression Material that Crosslinks by Means of a Condensation Reaction According to the Prior Art (Commercial Product)

A silicone dental material that crosslinks by means of a condensation reaction (commercial product Lastic 90 fine, Kettenbach GmbH+Co. KG, lot 91631/91841) is mixed homogeneously using a mixing spatula on a mixing block according to the manufacturer's instructions.

Result, Comparative Example BV1:

The equilibrium contact angles between 40 and 120 seconds of age of the material (after the start of mixing of the catalyst component and the basic component) was between 90° and 105° when measured 10 seconds after applying the water droplet. This comparative example shows that silicone dental impression materials that crosslink by means of a condensation reaction according to the prior art do not lead to the inventive effect of a spontaneous spreading of an applied water droplet on the surface of the dental impression material.

TABLE 3

Time-dependent contact angle measurements on silicones that crosslink by means of a condensation reaction and contain an inventive synergistic surfactant mixture in comparison with the prior art

| Examples/ Comparative examples | Age of material after start of mixing 40 s[1] Period of time until reaching a contact angle of 10°[2] (s) | Age of material after start of mixing 60 s[1] Period of time until reaching a contact angle of 10°[2] (s) | Age of material after start of mixing 90 s[1] Period of time until reaching a contact angle of 10°[2] (s) | Age of material after start of mixing 120 s[1] Period of time until reaching a contact angle of 10°[2] (s) |
|---|---|---|---|---|
| Example B1 | 0.5 | 0.5 | 0.6 | 0.4 |
| Comparative example BV1 | —[3] | —[3] | —[3] | —[3] |

[1] Time of placement of the droplet of water after the start of mixing of the impression material
[2] Droplet size approximately 8 µL, measurement time of droplet max. 20 s
[3] No contact angle <10° is achieved within the measurement time of 20 s after applying the droplet of water

TABLE 4

Time-dependent contact angle measurements on silicones that crosslink by means of a condensation reaction and contain an inventive synergistic surfactant mixture in comparison with the prior art

| Examples/ Comparative examples | Age of material after start of mixing 40 s[1] Age of droplet 10 s[2] Contact angle (°) | Age of material after start of mixing 60 s[1] Age of droplet 10 s[2] Contact angle (°) | Age of material after start of mixing 90 s[1] Age of droplet 10 s[2] Contact angle (°) | Age of material after start of mixing 120 s[1] Age of droplet 10 s[2] Contact angle (°) |
|---|---|---|---|---|
| Example B1 | <10 | <10 | <10 | <10 |
| Comparative example BV1 | 90 | 94 | 101 | 105 |

[1] Time of placement of the droplet of water after the start of mixing of the impression material
[2] Droplet size approximately 8 µL, measurement time of droplet max. 20 s C) Alkoxysilyl Polyether Dental Impression Material that Crosslinks by Means of a Condensation Reaction S Synthesis Example C1

Basic Compound of a Alkoxysilyl Polyether Dental Impression Material that Crosslinks by Means of a Condensation Reaction with an Inventive Synergistic Surfactant Mixture 94 parts of a basic compound of a alkoxysilyl polyether dental impression material that crosslinks by means of a condensation reaction according to EP-A-1 226 808 (commercial product P2-Polyether mono, Heraeus-Kulzer, lot #290489) were mixed homogeneously for 15 minutes and degassed in a vacuum mixer with 3.00 parts of a perfluoropolyether surfactant (Fluorolink E10 H from Solvay Solexis) with a surface tension of 23 dyn/cm at 20° and a molecular weight of approximately 1500 g/mol, 3.00 parts of a polyethylene oxide-modified polydimethylsiloxane (PEG-8 methicone) with a surface tension of 20.7 dyn/cm (in deionized water at 25° C. at a concentration of 1%) and a molecular weight of approximately 620 g/mol. A moderately fluid paste (ISO 4823) was obtained. The paste is a possible basic component of the inventive two-component dental impression compound.

Example C1

Alkoxysilyl Polyether Dental Impression Material that Crosslinks by Means of a Condensation Reaction with an Inventive Synergistic Surfactant Mixture 16.7 parts of a catalyst paste of a alkoxysilyl polyether dental impression material that crosslinks by means of a condensation reaction according to EP-A-1 226 808 (commercial product P2-Polyether mono, Heraeus-Kulzer, lot #290489) and 83.3 parts of the basic component described in synthesis example C1 were each dispensed from tube bags with the help of an electric dispensing device (Plug+Press Dispenser, Kettenbach GmbH+Co. KG) and mixed homogeneously using a dynamic mixer (Heraeus-Kulzer).
Result, Example C1:
A moderately fluid dental impression compound (ISO 4823) was obtained, and its contact angle was determined at various points in time within the processing time (see Tables 5 and 6). It was found that in each phase during the processing time of the impression compound, a droplet of water applied would spread completely on the surface of the impression compound and wet it within ≤10 seconds. Such a material is excellently suited for flowing on the areas to be molded in the patient's mouth, despite the influence of moist dental substance and saliva, and is capable of imaging it accurately in the impression. In contrast with commercial alkoxysilyl dental impression materials that crosslink by means of a condensation reaction (comparative example CV1) and have not been provided with the inventive synergistic surfactant mixture, there is a significant difference in the behavior of an applied water droplet on the surface of the impression material. With the addition of the synergistic surfactant mixture, an applied water droplet will spread completely on the surface of the impression compound within ≤10 seconds and wet it in each phase during the processing time of the impression compound, but with the unmodified commercial product, the applied water droplets do not spread on the surface of the impression compound and do not adequately wet it. In contrast with the conventional dental impression materials available on the market, the inventive material is excellently suited for flowing on the areas to be molded in the patient's mouth despite the influence of moist dental substance, saliva and blood, and imaging these areas accurately in the impression.

Comparative Example CV1

Alkoxysilyl Polyether Dental Impression Material that Crosslinks by Means of a Condensation Reaction According to the Prior Art (Commercial Product)

A alkoxysilyl polyether dental impression material that crosslinks by means of a condensation reaction according to EP-A-1 226 808 (commercial product P2-Polyether mono, Heraeus-Kulzer, lot #290489) is dispensed from tube bags with the help of an electric dispensing device (Plug+Press Dispenser, Kettenbach GmbH+Co. KG) according to the manufacturer's instructions and mixed homogeneously using a dynamic mixer (Heraeus-Kulzer).
Result, Comparative Example CV1:
The equilibrium contact angles between 40 and 120 seconds of age of the material (after the start of mixing of the catalyst component and the basic component) was between 62° and 66° when measured 10 seconds after applying the water droplet. This comparative example shows that alkoxysilyl polyether dental impression material that crosslinks by means of a condensation reaction s according to the prior art do not lead to the inventive effect of a spontaneous spreading of an applied water droplet on the surface of the dental impression material.

TABLE 5

Time-dependent contact angle measurements on alkoxysilyl polyethers that crosslink by means of a condensation reaction with an inventive synergistic surfactant mixture in comparison with the prior art

| Examples/ Comparative examples | Age of material after start of mixing 40 s[1]) Period of time until reaching a contact angle of 10°[2]) (s) | Age of material after start of mixing 60 s[1]) Period of time until reaching a contact angle of 10°[2]) (s) | Age of material after start of mixing 90 s[1]) Period of time until reaching a contact angle of 10°[2]) (s) | Age of material after start of mixing 120 s[1]) Period of time until reaching a contact angle of 10°[2]) (s) |
|---|---|---|---|---|
| Example C1 | 0.25 | 0.25 | 0.25 | 0.25 |
| Comparative example CV1 | —[3]) | —[3]) | —[3]) | —[3]) |

[1])Time of placement of the droplet of water after the start of mixing of the impression material
[2])Droplet size approximately 8 μL, measurement time of droplet max. 20 s
[3])No contact angle <10° is achieved within the measurement time of 20 s after applying the droplet of water

TABLE 6

Time-dependent contact angle measurements on alkoxysilyl polyethers that crosslink by means of a condensation reaction with an inventive synergistic surfactant mixture in comparison with the prior art

| Examples/ Comparative examples | Age of material after start of mixing 40 s[1]) Age of droplet 10 s[2]) Contact angle (°) | Age of material after start of mixing 60 s[1]) Age of droplet 10 s[2]) Contact angle (°) | Age of material after start of mixing 90 s[1]) Age of droplet 10 s[2]) Contact angle (°) | Age of material after start of mixing 120 s[1]) Age of droplet 10 s[2]) Contact angle (°) |
|---|---|---|---|---|
| Example C1 | <10 | <10 | <10 | <10 |
| Comparative example CV1 | 64 | 62 | 66 | 65 |

[1])Time of placement of the droplet of water after the start of mixing of the impression material
[2])Droplet size approximately 8 μL, measurement time of droplet max. 20 s D) Aziridino Polyether Dental Impression Materials that Crosslink by Means of an Addition Reaction Synthesis Example D1

Basic Compound of an Aziridino Polyether Dental Impression Material that Crosslinks by Means of an Addition Reaction and Contains an Inventive Synergistic Surfactant Mixture 97.6 parts of a basic compound of an aziridino polyether dental impression material that crosslinks by means of an addition reaction according to U.S. Pat. No. 4,353,242 (commercial product Impregum Penta, 3M-Espe, lot 347351) were mixed homogeneously for 15 minutes and degassed in a vacuum mixer with 0.45 part of a perfluoropolyether surfactant (Fluorolink E10 H from Solvay Solexis) with a surface tension of 23 dyn/cm at 20° and a molecular weight of approximately 1500 g/mol, 1.35 parts of a polyethylene oxide-modified polydimethylsiloxane (PEG-8 methicone) with a surface tension of 20.7 dyn/cm (in deionized water at 25° C. at a concentration of 1%) and a molecular weight of approximately 620 g/mol and 0.6 part glycerol. A moderately fluid paste (ISO 4823) was obtained. The paste is a possible basic component of the inventive two-component dental impression compound.

Example D1

Aziridino Polyether Dental Impression Material that Crosslinks by Means of an Addition Reaction with an Inventive Synergistic Surfactant Mixture 16.7 parts of a catalyst paste of an aziridino polyether dental impression material that crosslinks by means of an addition reaction according to U.S. Pat. No. 4,353,242 (commercial product Impregum Penta, 3M-Espe, lot 346743) and 83.3 parts of the basic component described in synthesis example D1 were each dispensed from tube bags with the help of an electric dispensing device (Plug+Press Dispenser, Kettenbach GmbH+Co. KG) and mixed homogeneously using a dynamic mixer (3M-Espe).

Result, Example D1:

A moderately fluid dental impression compound (ISO 4823) was obtained, and its contact angle was determined at various points in time within the processing time (see Tables 7 and 8). It was found that in each phase during the processing time of the impression compound, a droplet of water applied would spread completely on the surface of the impression compound and wet it within ≤10 seconds. Such a material is excellently suited for flowing on the areas to be molded in the patient's mouth, despite the influence of moist dental substance and saliva, and is capable of imaging it accurately in the impression. In contrast with commercial aziridino polyether dental impression materials that crosslink by means of an addition reaction (comparative example DV1) and have not been provided with the inventive synergistic surfactant mixture, there is a significant difference in the behavior of an applied water droplet on the surface of the impression material. With the addition of the synergistic surfactant mixture an applied water droplet will spread completely on the surface of the impression compound within ≤10 seconds and wet it in each phase during the processing time of the impression compound, with the unmodified commercial product, the applied water droplets do not spread on the surface of the impression compound and do not adequately wet it. The inventive material is excellently suited, in contrast with the conventional dental impression materials available on the market, for flowing on the areas to be molded in the patient's mouth despite the influence of moist dental substance, saliva and blood, and imaging these areas accurately in the impression.

Comparative Example DV1

Aziridino Polyether Dental Impression Material that Crosslinks by Means of an Addition Reaction According to the Prior Art (Commercial Product)

An aziridino polyether dental impression material that crosslinks by means of an addition reaction according to U.S. Pat. No. 4,353,242 (commercial product Impregum Penta, 3M-Espe, lot 347351/346743) is dispensed from tube bags by using an electric dispensing device (Plug+Press Dispenser, Kettenbach GmbH+Co. KG) according to the manufacturer's instructions and mixed homogeneously.

Result, Comparative Example DV1:

The equilibrium contact angles between 40 and 120 seconds of age of the material (after the start of mixing of the catalyst component and the basic component) was between 53° and 5° when measured 10 seconds after applying the water droplet. This comparative example shows that aziridino polyether dental impression materials that crosslink by means of an addition reaction according to the prior art do not lead to the inventive effect of a spontaneous spreading of an applied water droplet on the surface of the dental impression material.

TABLE 7

Time-dependent contact angle measurements on aziridino polyether that crosslinks by means of an addition reaction and contains an inventive synergistic surfactant mixture in comparison with the prior art

| Examples/ Comparative example | Age of material after start of mixing 40 s[1] Period of time until reaching a contact angle of 10°[2] (s) | Age of material after start of mixing 60 s[1] Period of time until reaching a contact angle of 10°[2] (s) | Age of material after start of mixing 90 s[1] Period of time until reaching a contact angle of 10°[2] (s) | Age of material after start of mixing 120 s[1] Period of time until reaching a contact angle of 10°[2] (s) |
|---|---|---|---|---|
| Example D1 | 12.5 | 10 | 10 | 10 |
| Comparative example CV1 [sic] | —[3] | —[3] | —[3] | —[3] |

[1] Time of placement of the droplet of water after the start of mixing of the impression material
[2] Droplet size approximately 8 μL, measurement time of droplet max. 20 s
[3] No contact angle <10° is achieved within the measurement time of 20 s after applying the droplet of water

TABLE 8

Time-dependent contact angle measurements on aziridino polyether that crosslinks by means of an addition reaction and contains an inventive synergistic surfactant mixture in comparison with the prior art

| Examples/ Comparative examples | Age of material after start of mixing 40 s[1] Age of droplet 10 s[2] Contact angle (°) | Age of material after start of mixing 60 s[1] Age of droplet 10 s[2] Contact angle (°) | Age of material after start of mixing 90 s[1] Age of droplet 10 s[2] Contact angle (°) | Age of material after start of mixing 120 s[1] Age of droplet 10 s[2] Contact angle (°) |
|---|---|---|---|---|
| Example D1 | <10 | <10 | <10 | <10 |
| Comparative example DV1 | 53 | 53 | 56 | 58 |

[1] Time of placement of the droplet of water after the start of mixing of the impression material
[2] Droplet size approximately 8 μL, measurement time of droplet max. 20 s The inventive examples and the comparative examples from the prior art show that not any combination of fluorosurfactants and silicone surfactants leads to a synergistic effect in the sense of the present invention. Even if the best surfactants each from the experimental series of silicone surfactants and fluorosurfactants from the prior art are combined, there is still no spreading of water droplets on the surface of the silicone impression material.

In contrast with that, a synergistic effect has surprisingly been achieved only in surfactant mixtures with certain fluorosurfactants and silicone surfactants according to the present invention.

The invention claimed is:

1. A composition containing one or more curable polymers selected from the group of organopolysiloxanes that crosslink by means of an addition reaction, organopolysiloxanes that crosslink by means of a condensation reaction, polyethers that contain alkoxysilyl groups and crosslink by means of a condensation reaction, polyethers that contain aziridino groups and crosslink by means of an addition reaction, polyethers that contain alkenyl groups and crosslink by means of an addition reaction, polyethers that contain ester groups of an ethylenically unsaturated carboxylic acid and crosslink by means of a radical polymerization reaction, or polyethers, silicones or rubbers that crosslink by means of a ring-opening metathesis reaction and also containing at least one nonionic surfactant having silicon-containing groups with a molecular weight of less than 6000 g/mol, as well as also containing at least one fluorosurfactant which is a block copolymer containing blocks of formula Ia

where $R_F$ is a partially fluorinated or perfluorinated alkylene group with 2 to 12 carbon atoms, wherein the number of carbon atoms of the partially fluorinated or perfluorinated alkylene groups within a polyether group may vary within the scope of the given definitions, $R_H$ denotes an alkylene group with 2 to 12, wherein the number of carbon atoms of the alkylene groups within a polyether group may vary within the scope of the given definitions, A' is a covalent bond or a divalent bridge group, which is linked to the blocks [O—$R_F$] and [O—$R_H$] by C—C and/or C—O bonds, a is an integer from 2 to 200, and d is an integer from 1 to 200.

2. The composition according to claim 1, characterized in that $R_H$ denotes an alkylene group with 2 to 6 carbon atoms, wherein the number of carbon atoms of the alkylene groups within a polyether group may vary within the scope of the given definitions, A' is a covalent bond or a divalent bridge group, which is linked to the blocks [O—$R_F$] and [O—$R_H$] by C—C and/or C—O bonds, a is an integer from 2 to 50, and d is an integer from 1 to 50.

3. The composition according to claim 1, characterized in that the fluorosurfactant is a compound of formula Ib

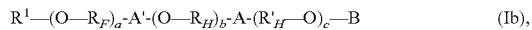

where $R^1$ is hydrogen, a partially fluorinated or perfluorinated alkyl group with 1 to 6 carbon atoms or an alkyl group with 1 to 6 carbon atoms, $R_F$ has the meaning defined in claim 1, $R_H$ and $R'_H$, independently of one another, denote alkylene groups with 2 to 12, wherein the number of carbon atoms of the alkylene groups within a polyether group may vary within the scope of the given definitions, A and A' independently of one another denote a covalent bond or a divalent bridge group, which is linked to the blocks [O—$R_F$], [O—$R_H$] and [$R'_H$—O] via C—C and/or C—O bonds, a denotes an integer from 2 to 200, b denotes an integer from 0 to 100, c denotes an integer from 1 to 100 and B denotes hydrogen, alkyl, partial fluoroalkyl or perfluoroalkyl.

4. The composition according to claim 1, characterized in that the fluorosurfactant is a block copolymer of formulas Ic or Id

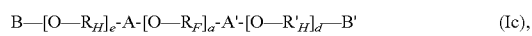

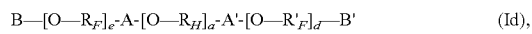

where

A and A', independently of one another, denote a covalent bond or divalent bridge group, which is linked to the blocks [O—$R_F$], [O—$R_H$] and [O—$R'_H$] via C—C and/or C—O bonds, B and B', independently of one another, denote hydrogen, a partially fluorinated or perfluorinated alkyl group with 1 to 6 carbon atoms or an alkyl group with 1 to 6 carbon atoms, $R_F$ denotes a group of formula —$C_mF_nH_o$—, where the indices m, n and o may be different within one polyether group within the scope of the given definitions, $R'_F$ is a group of formula —$C_{m'}F_{n'}H_{o'}$—, where the indices m, n and o may be different within one polyether group within the scope of the given definitions, m and m', independently of one another, denote integers from 2 to 12, n and n', independently of one another, denote integers from 1 to 24, o and o', independently of one another, denote integers from 0 to 23, where the sum of n and o corresponds to the value of 2m, $R_H$ is a group of the formula —$C_pH_{2p}$—, where the index p may be different in one polyether group within the scope of the given definition, $R'_H$ is a group of formula —$C_qH_{2q}$—, where the index q may be different within the scope of the given definition in one polyether group, p is an integer from 2 to 12, q is an integer from 2 to 12, a is an integer from 2 to 100, d is an integer from 1 to 100, and e is an integer from 1 to 100.

5. The composition according to claim 4, characterized in that the fluorosurfactant is a block copolymer of formula Ica

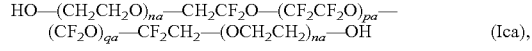

where na is an integer from 1 to 20, pa is an integer from 0 to 12, and qa is an integer from 0 to 20, with the provision that the sum of pa and qa must be at least 1.

6. The composition as specified in claim 1, characterized in that in addition to containing the fluorosurfactant of claim 1, it also contains other ionic and/or nonionic and/or amphoteric fluorosurfactants.

7. The composition as specified in claim 1, characterized in that the silicon-containing nonionic surfactant containing at least one (poly)alkylene oxide group has a molecular weight of less than 4000 g/mol.

8. The composition as specified in claim 1, characterized in that the silicon-containing nonionic surfactant is an organosiloxane surfactant of formula II and/or formula III or an organocarbosilane surfactant or formulas IV, V and/or VI

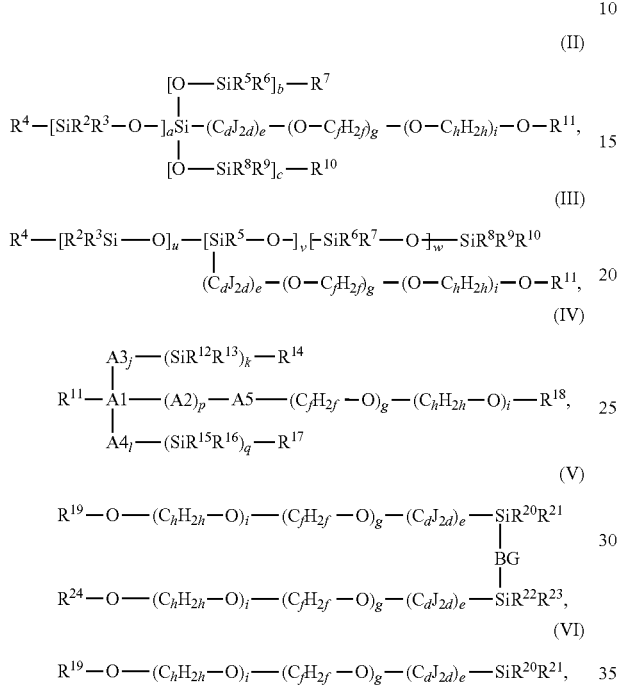

where $R^2$, $R^3$, $R^4$, $R^5$, $R^6$, $R^7$, $R^8$, $R^9$ and $R^{10}$, independently of one another, denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are optionally either partially or completely fluorinated, a, b, c and w, independently of one another, are integers from 0 to 100, v is an integer from 1 to 100, where the sum of a, b and c is between 1 and 300, and the sum of v and w is between 1 and 200, u is 0 or 1, d is an integer from 1 to 10, J is hydrogen or fluorine, e is 0 or 1, f and h, independently of one another, are integers from 2 to 6, g and i, independently of one another, are integers from 0 to 30, where the sum of g and i is 1 to 60, $R^{11}$ is hydrogen, alkyl, alkenyl or aryl, optionally partially or completely fluorinated, $R^{12}$, $R^{13}$, $R^{14}$, $R^{15}$, $R^{16}$ and $R^{17}$, independently of one another, denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are optionally partially or completely fluorinated, k and q independently of one another are 0 or 1, A1 is carbon or silicon, A2, A3 and A4 independently of one another are a group $C_dJ_{2d}$, where J and d have the meanings defined above, j, p and l, independently of one another, are 0 or 1, A5 is a divalent bridge group, $R^{18}$ is hydrogen, alkyl, alkenyl or aryl, optionally partially or completely fluorinated, $R^{20}$, $R^{21}$, $R^{22}$ and $R^{23}$, independently of one another, denote hydrogen, alkyl, alkyloxy, alkenyl, alkenyloxy, alkynyl, alkynyloxy, aryl, aryloxy, aralkyl, aralkyloxy, alkylaryl and/or alkylaryloxy, optionally partially or completely fluorinated, BG is a divalent bridge group, and $R^{19}$ and $R^{24}$ independently of one another denote hydrogen, alkyl, alkenyl or aryl, optionally partially or completely fluorinated, with the provision that of the groups $R^2$, $R^3$ and $R^4$ and/or the groups $R^5$, $R^6$ and $R^7$ and/or the groups $R^8$, $R^9$ and $R^{10}$ and/or the groups $R^{15}$, $R^{16}$ and $R^{17}$ and/or the groups $R^{20}$ and $R^{21}$ and/or the groups $R^{22}$ and $R^{23}$ and/or the groups $R^{20}$, $R^{21}$ and $R^{22}$ only one can be hydrogen, where f and h may assume different values within one molecule within the scope of the given definition.

9. The composition as specified in claim 1, characterized in that the silicon-containing nonionic surfactant containing at least one (poly)alkylene oxide group is a compound of formulas VII, VIII, IX or X

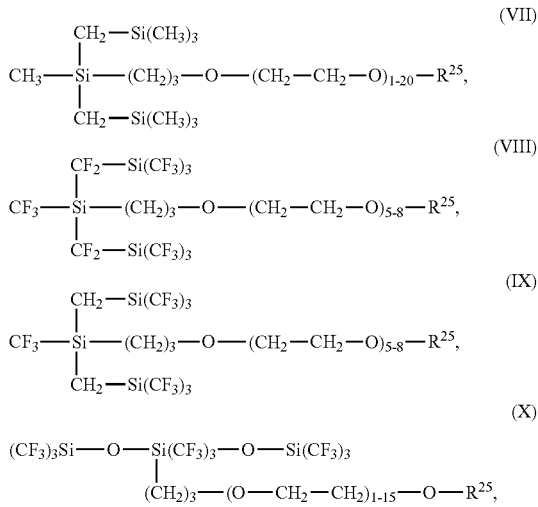

where $R^{25}$ is hydrogen, methyl, ethyl, propyl or butyl.

10. The composition as specified in claim 1, characterized in that in addition to containing the at least one fluorosurfactant of claim 1, it also contains as an additional component a polyether containing alkenyl groups and/or alkynyl groups and/or a hydroxyl- and/or aryloxy- and/or arylalkoxy- and/or alkoxy-terminated polyether.

11. The composition as specified in claim 1, characterized in that, in addition to the at least one fluorosurfactant of claim 1, it also contains a polyol as an additional component.

12. The composition according to claim 11, characterized in that it contains as an additional component, a polyether containing alkenyl groups and/or alkynyl groups and/or an aryloxy- and/or arylalkyloxy- and/or hydroxyl- and/or alkoxy-terminated polyether.

13. The composition according to claim 11 wherein the polyol is selected from the group of carbohydrates, polyvinyl alcohols, aliphatic diols, triols, tetraols, pentaols and/or hexaols and mixtures of two or more of these polyols.

14. The composition according to claim 11, characterized in that the polyol is selected from the group of polyvinyl alcohols, polysaccharides, trimethylol propane, pentaerythritol, dipentaerythritol, glycerol, allyloxy-1,2-propanediol, 2-methyl-2,4-pentanediol, trimethylolpropane allyl ether, decanediol, nonanediol, octanediol, heptanediol, hexanediol, pentanediol, butanediol, propanediol, ethanediol, fructose, glucose and mixtures of two or more of these polyols.

15. The composition according to claim 10, characterized in that the polyether containing the alkenyl groups is a compound of formula XII, and the hydroxyl-terminated and/or alkoxy-terminated polyether is a compound of formula XIII

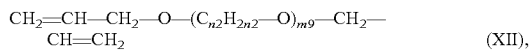

(XII),

(XIII), where n2 denotes an integer from 2 to 8,
m9 is an integer from 3 to 70,000,
$R^{31}$ and $R^{32}$, independently of one another, denote hydrogen or $C_1$-$C_6$ alkyl, and
where $R^{31}$, $R^{32}$, n2 and m9 may be different within one molecule within the scope of the given definition.

16. The composition according to claim 6, characterized in that the weight ratio of fluorosurfactants of claim 1 to other fluorosurfactants is 100:1 to 1:100.

17. The composition according to claim 1, characterized in that the weight ratio of silicon-containing surfactant to fluorosurfactant, is 100:1 to 1:100.

18. The composition as specified in claim 1, characterized in that it is an organopolysiloxane multicomponent dental impression compound that crosslinks by means of an addition reaction and contains components A and B, wherein
   a) component A contains an organopolysiloxane with at least 2 ethylenically unsaturated groups and a hydrosilylation catalyst,
   b) component B contains an organohydrogen polysiloxane, and
   c) at least one of components A and/or B contains the fluorosurfactant of claim 1 in combination with a nonionic surfactant having silicon-containing groups.

19. The composition as specified in claim 1, characterized in that it contains one or more fillers in a total amount of 0.01 to 80 wt %.

20. The composition as specified in claim 1, characterized in that it contains one or more of the following additives: buffer salts, water scavengers, paste forming agents, additional surfactants, active ingredients, plasticizers, optical scan-enabling substances, taste and/or odor substances, diagnostics-enabling substances, fluoridation agents, bleach substances, desensitizers, adhesion promoters, dyes, indicators, stabilizers (antioxidants) and antibacterial substances.

21. The composition according to claim 1, characterized in that it contains
   a) 10 wt % to 85 wt % organopolydialkylsiloxane with at least 2 alkenyl groups,
   b) 1 to 70 wt % organohydrogen polysiloxane with an SiH content of 0.1 to 15.0 mmol/g,
   c) 0.0001 to 2 wt % hydrosilylation catalyst,
   d) 0 to 90 wt % nonreinforcing fillers with a BET surface area of less than 50 m²/g,
   e) 0.1 to 50 wt % reinforcing fillers with a BET surface area equal to or greater than 50 m²/g,
   f) 0 to 20 wt % auxiliaries and additives,
   g) 0.01 to 10.0 wt % of a nonionic surfactant having at least one (poly)alkylene oxide group and a silicon-containing group and having a molecular weight of less than 6000 g/mol, which is a nonionic polyether siloxane surfactant with 3 to 7 silicon atoms in the siloxane substructure and/or nonionic polyether carbosilane surfactant with 1 to 7 silicon atoms in the carbosilane substructure and an alkylene oxide content of 1 to 20 units, and
   h) 0.001 to 10.0 wt % of the at least one fluorosurfactant, according to claim 1.

22. The composition according to claim 21, characterized in that it additionally contains i) 0.1 to 25 wt % branched or linear alkyl-, hydroxy-, alkynyl- and/or alkenyl-terminated polyalkylene ethers and/or mixtures thereof.

23. The composition according to claim 22, characterized in that it is a two-component dental impression compound consisting of components A and B, where component A contains
   a) 10 to 80 wt % organopolydialkylsiloxane with at least 2 alkenyl groups,
   c) 0.0001 to 2 wt % hydrosilylation catalyst,
   d) 0 to 90 wt % nonreinforcing fillers with a BET surface area of less than 50 m²/g,
   e) 0.1 to 50 wt % reinforcing fillers with a BET surface area of greater than or equal to 50 m²/g,
   f) 0 to 20 wt % auxiliaries and additives, and
   j) 0.001 to 5.0 wt % alkyl-, aryl- or aralkyl-capped nonionic surfactants,
   and component B contains
   a) 0.1 to 70 wt % organopolydialkylsiloxane with at least 2 alkenyl groups,
   b) 1.2 to 80 wt % organohydrogen polysiloxane with an SiH content of 0.1 to 15.0 mmol/g,
   d) 0 to 90 wt % nonreinforcing fillers with a BET surface area of less than 50 m²/g,
   e) 0.1 to 50 wt % reinforcing fillers with a BET surface area greater than or equal to 50 m²/kg,
   f) 0 to 20 wt % auxiliaries and additives,
   g) 0.01 to 10.0 wt % of a nonionic surfactant containing at least one (poly)alkylene oxide group and one silicon-containing group and having a molecular weight of less than 6000 g/mol, which is a nonionic polyether siloxane surfactant with 3 to 7 silicon atoms in the siloxane substructure and/or a nonionic polyether carbosilane surfactant with 1 to 7 silicon atoms in the carbosilane substructure and an alkylene oxide content of 1 to 20 units,
   h) 0.001 to 10.0 wt % of the at least one fluorosurfactants according to claim 1, and
   i) 0.5 to 50 wt % branched or linear alkyl or alkynyl and/or alkenyl and/or hydroxy-terminated (poly)alkylene ethers and/or mixtures thereof.

24. The composition according to claim 23, characterized in that it is a two-component dental impression compound, consisting of components A and B, where component A contains
   a) 10 to 80 wt % organopolydialkylsiloxane with at least 2 alkenyl groups,
   c) 0.01 to 2 wt % hydrosilylation catalyst,
   d) 0 to 90 wt % nonreinforcing fillers with a BET surface area of less than 50 m²/g,
   e) 0.1 to 50 wt % reinforcing fillers with a BET surface area greater than or equal to 50 m²/kg,
   f) 0 to 20 wt % auxiliaries and additives, and
   j) 0.001 to 5.0 wt % alkyl-, aryl- or aralkyl-capped nonionic surfactants,
   and component B contains
   a) 0.1 to 70 wt % organopolydialkylsiloxane with at least 2 alkenyl groups,
   b) 1.2 to 80 wt % organohydrogen polysiloxane with an SiH content of 0.1 to 15.0 mmol/g,
   e) 0 to 90 wt % nonreinforcing fillers with a BET surface area of less than 50 m²/g, f) 0.1 to 50 wt % reinforcing fillers with a BET surface area greater than or equal to 50 m²/kg, g) 0 to 20 wt % auxiliaries and additives, h) 0.01 to 10.0 wt % nonionic polyether siloxane surfactant with 3 to 7 silicon atoms in the siloxane substructure and/or nonionic polyether carbosilane surfactant with 1 to 7 silicon atoms in the carbosilane substructure and an alkylene oxide content of 1 to 20 units, i) 0.001 to 10.0 wt % of the fluorosurfactant, according to claim 1, and k) 0.5 to 50 wt % polyol or mixtures of polyols.

25. The composition as specified in claim 1, characterized in that has a low initial water droplet contact angle of <10° measured at a droplet age of 10 seconds, 40 seconds after the start of mixing.

26. The composition according to claim 25, characterized in that the water droplet contact angle 40 seconds after the start of mixing assumes the following values: after a droplet age of 0.25 second, a water droplet contact angle of <75°; after a droplet age of 0.5 second, a water droplet contact angle of <55°; after a droplet age of 1 second, a water droplet contact angle of <35'; after a droplet age of 2 seconds, a water droplet contact angle of <20'; and after a droplet age of 3 seconds, a water droplet contact angle of <10°.

27. A mixture obtained by mixing the compositions according to claim 1.

28. A curable impression material obtained by curing the composition according to claim 1.

29. A dental impression compound comprising a fluorosurfactant, according to claim 1 with at least one silicon-containing nonionic surfactant having at least one (poly)alkylene oxide group and a molecular weight of less than 6000 g/mol, optionally in combination with at least one additional fluorosurfactant.

30. A method for making a cured dental material, the method comprising curing a composition according to claim 1.

* * * * *